United States Patent
Fujisawa et al.

(10) Patent No.: US 8,779,178 B2
(45) Date of Patent: Jul. 15, 2014

(54) HYDROLYSIS-RESISTANT SILICONE COMPOUNDS

(71) Applicants: Johnson & Johnson Vision Care, Inc., Jacksonville, FL (US); Toray Industries, Inc., Tokyo (JP)

(72) Inventors: Kazuhiko Fujisawa, Otsu (JP); Masataka Nakamura, Otsu (JP); Yokota Yokota, Otsu (JP); Douglas G. Vanderlaan, Jacksonville, FL (US)

(73) Assignees: Johnson & Johnson Vision Care, Inc., Jacksonville, FL (US); Toray Industries, Inc., Tokyo (JP)

( * ) Notice: Subject to any disclaimer, the term of this patent is extended or adjusted under 35 U.S.C. 154(b) by 0 days.

(21) Appl. No.: 13/746,265

(22) Filed: Jan. 21, 2013

(65) Prior Publication Data

US 2013/0131369 A1   May 23, 2013

Related U.S. Application Data

(60) Division of application No. 12/901,191, filed on Oct. 8, 2010, now Pat. No. 8,357,818, which is a continuation of application No. 11/561,456, filed on Nov. 20, 2006, now Pat. No. 7,838,698.

(60) Provisional application No. 60/848,317, filed on Sep. 29, 2006.

(51) Int. Cl.
   *C07F 7/00* (2006.01)

(52) U.S. Cl.
   USPC .......................................................... 556/443

(58) Field of Classification Search
   USPC .......................................................... 556/443
   See application file for complete search history.

(56) References Cited

U.S. PATENT DOCUMENTS

| | | |
|---|---|---|
| 2,793,223 A | 5/1957 | Merker |
| 2,956,044 A | 10/1960 | Merker |
| 3,001,975 A | 9/1961 | O'Brien |
| 3,057,902 A | 10/1962 | Pike |
| 3,377,371 A | 4/1968 | Quall et al. |
| 3,563,742 A | 2/1971 | Kempen |
| 3,699,081 A | 10/1972 | Iwashita |
| 3,756,820 A | 9/1973 | Hayakawa et al. |
| 3,808,178 A | 4/1974 | Gaylord et al. |
| 3,859,320 A | 1/1975 | Atherton |
| 3,865,588 A | 2/1975 | Ohto et al. |
| 3,959,358 A | 5/1976 | Jursich |
| 4,117,001 A | 9/1978 | Fozzard |
| 4,120,570 A | 10/1978 | Gaylord |
| 4,139,513 A | 2/1979 | Tanaka et al. |
| 4,139,692 A | 2/1979 | Tanaka et al. |
| 4,144,137 A | 3/1979 | Stewart |
| 4,235,985 A | 11/1980 | Tanaka et al. |
| 4,246,389 A | 1/1981 | LeBoeuf |
| 4,259,467 A | 3/1981 | Keogh et al. |
| 4,260,725 A | 4/1981 | Keogh et al. |
| 4,321,029 A | 3/1982 | Aoki |
| 4,395,496 A | 7/1983 | Wittmann et al. |
| 4,402,887 A | 9/1983 | Kuriyama et al. |
| 4,463,149 A | 7/1984 | Ellis |
| 4,563,538 A | 1/1986 | Wakabayashi et al. |
| 4,602,074 A | 7/1986 | Mizutani et al. |
| 4,632,968 A | 12/1986 | Yokota et al. |
| 4,853,453 A | 8/1989 | Schafer et al. |
| 4,861,850 A | 8/1989 | Novicky |
| 5,010,141 A | 4/1991 | Mueller |
| 5,045,233 A | 9/1991 | Kita et al. |
| 5,045,621 A | 9/1991 | Suzuki |
| 5,057,578 A | 10/1991 | Spinelli |
| 5,079,319 A | 1/1992 | Mueller |
| 5,128,484 A | 7/1992 | Kita et al. |
| 5,219,965 A | 6/1993 | Valint, Jr. et al. |
| 5,244,981 A | 9/1993 | Seidner et al. |
| 5,314,960 A | 5/1994 | Spinelli et al. |
| 5,321,108 A | 6/1994 | Kunzler et al. |
| 5,329,034 A | 7/1994 | Nagase et al. |
| 5,336,797 A | 8/1994 | McGee et al. |

(Continued)

FOREIGN PATENT DOCUMENTS

| | | |
|---|---|---|
| BR | 7403534 | 4/1974 |
| EP | 0300620 A1 | 1/1989 |
| EP | 0306756 A2 | 3/1989 |
| EP | 0639576 A1 | 2/1995 |
| EP | 0 733 637 A1 | 9/1996 |

(Continued)

OTHER PUBLICATIONS

Issue Notification issued on Feb. 9, 2011 for U.S. Appl. No. 12/060,536, filed Apr. 1, 2008 (Applicant—Vistakon; Inventors—Fujisawa, et al.) (1 page).

Response to Amendment issued on Jan. 14, 2011 for U.S. Appl. No. 12/060,536, filed Apr. 1, 2008 (Applicant—Vistakon; Inventors—Fujisawa, et al.) (2 pages).

Amendment after Notice of Allowance filed on Dec. 1, 2010 for; U.S. Appl. No. 12/060,536, filed Apr. 1, 2008 (Applicant—Vistakon; Inventors—Fujisawa, et al.) (2 pages).

(Continued)

*Primary Examiner* — Porfirio Nazario Gonzalez
*Assistant Examiner* — Kofi Adzamli
(74) *Attorney, Agent, or Firm* — Ballard Spahr LLP

(57) ABSTRACT

In one aspect, the invention relates to hydrolysis-resistant silicone compounds. In particular, disclosed are sterically hindered hydrolysis-resistant silicone compounds and improved purity hydrolysis-resistant silicone compounds. Also disclosed are processes for making hydrolysis-resistant silicone compounds; the products of the disclosed processes; compositions and polymers comprising the disclosed compounds and products of the disclosed processes; and ophthalmic lenses, for example contact lenses, intraocular lenses, artificial cornea, and spectacle lenses, comprising the disclosed compositions, disclosed polymers, disclosed compounds, and products of the disclosed processes. This abstract is intended as a scanning tool for purposes of searching in the particular art and is not intended to be limiting of the present invention.

8 Claims, 2 Drawing Sheets

(56) References Cited

U.S. PATENT DOCUMENTS

| | | |
|---|---|---|
| 5,356,947 A | 10/1994 | Ali et al. |
| 5,371,147 A | 12/1994 | Spinelli et al. |
| 5,387,662 A | 2/1995 | Kunzler et al. |
| 5,387,663 A | 2/1995 | McGee et al. |
| 5,470,930 A | 11/1995 | Toba et al. |
| 5,481,015 A | 1/1996 | Nomura |
| 5,493,039 A | 2/1996 | Okawa et al. |
| 5,510,428 A | 4/1996 | Harano et al. |
| 5,539,016 A | 7/1996 | Kunzler et al. |
| 5,554,706 A | 9/1996 | Nagase et al. |
| 5,563,184 A | 10/1996 | McGee et al. |
| 5,610,252 A | 3/1997 | Bambury et al. |
| 5,831,110 A | 11/1998 | Isoda et al. |
| 5,888,356 A | 3/1999 | Keil et al. |
| 5,891,977 A | 4/1999 | Dietz et al. |
| 5,959,117 A | 9/1999 | Ozark et al. |
| 5,962,548 A | 10/1999 | Vanderlaan et al. |
| 5,994,488 A | 11/1999 | Yokota et al. |
| 6,031,059 A | 2/2000 | Vanderlaan et al. |
| 6,140,525 A * | 10/2000 | Okawa et al. ............... 556/434 |
| 6,177,585 B1 | 1/2001 | Chen et al. |
| 6,180,741 B1 | 1/2001 | Yamaguchi et al. |
| 6,218,503 B1 | 4/2001 | Lai et al. |
| 6,242,153 B1 | 6/2001 | Sato et al. |
| 6,306,992 B1 | 10/2001 | Yoshitake et al. |
| 6,334,935 B1 | 1/2002 | Uehara et al. |
| 6,344,495 B1 | 2/2002 | Ueda et al. |
| 6,350,816 B1 | 2/2002 | Farronato et al. |
| 6,372,815 B1 | 4/2002 | Sulc et al. |
| 6,617,373 B2 | 9/2003 | Sulc et al. |
| 6,649,722 B2 | 11/2003 | Rosenzweig et al. |
| 6,783,897 B2 | 8/2004 | Kang et al. |
| 6,787,615 B2 | 9/2004 | Keller et al. |
| 6,803,406 B2 | 10/2004 | Musa |
| 6,809,155 B2 | 10/2004 | Musa |
| 6,822,016 B2 | 11/2004 | McCabe et al. |
| 6,846,892 B2 | 1/2005 | Kindt-Larsen et al. |
| 6,908,969 B2 | 6/2005 | Musa |
| 6,922,118 B2 | 7/2005 | Kubena et al. |
| 6,933,401 B2 | 8/2005 | Molock et al. |
| 7,169,874 B2 | 1/2007 | Salamone et al. |
| RE39,635 E | 5/2007 | Vanderlaan et al. |
| 7,317,117 B2 | 1/2008 | Nakamura et al. |
| 7,368,589 B2 | 5/2008 | Mahadevan et al. |
| 7,461,937 B2 | 12/2008 | Steffen et al. |
| 7,838,698 B2 | 11/2010 | Fujisawa et al. |
| 2002/0016383 A1 | 2/2002 | Iwata et al. |
| 2003/0109661 A1 | 6/2003 | Salamone et al. |
| 2003/0125498 A1 | 7/2003 | McCabe et al. |
| 2003/0130465 A1 | 7/2003 | Lai et al. |
| 2003/0203986 A1 | 10/2003 | Valet |
| 2004/0014921 A1 | 1/2004 | Fujisawa et al. |
| 2004/0106694 A1 | 6/2004 | Fujisawa et al. |
| 2004/0114101 A1 | 6/2004 | Thakrar |
| 2004/0122249 A1 | 6/2004 | Fujisawa et al. |
| 2004/0198916 A1 | 10/2004 | Nakamura et al. |
| 2004/0198938 A1 | 10/2004 | Nakamura et al. |
| 2004/0201820 A1 | 10/2004 | Nakamura et al. |
| 2004/0249180 A1 | 12/2004 | Nakamura et al. |
| 2005/0165246 A1 | 7/2005 | Lai et al. |
| 2005/0179862 A1 | 8/2005 | Steffen et al. |
| 2005/0237483 A1 | 10/2005 | Phelan |
| 2006/0007391 A1 | 1/2006 | McCabe et al. |
| 2006/0036052 A1 | 2/2006 | Kindt-Larsen et al. |
| 2006/0047134 A1 | 3/2006 | Molock et al. |
| 2006/0223964 A1 | 10/2006 | Lai et al. |
| 2006/0229423 A1 | 10/2006 | Parakka et al. |
| 2007/0138669 A1 | 6/2007 | Lai et al. |
| 2007/0203275 A1 | 8/2007 | Kikuchi et al. |
| 2007/0242219 A1 | 10/2007 | Zanini et al. |
| 2008/0004383 A1 | 1/2008 | Nakamura et al. |
| 2008/0004401 A1 | 1/2008 | Nakamura et al. |
| 2008/0081850 A1 | 4/2008 | Fujisawa et al. |
| 2008/0081894 A1 | 4/2008 | Fujisawa et al. |
| 2008/0119627 A1 | 5/2008 | Nakamura et al. |
| 2008/0143003 A1 | 6/2008 | Phelan |
| 2008/0231798 A1 | 9/2008 | Zhou et al. |
| 2009/0005528 A1 | 1/2009 | Fujisawa et al. |
| 2009/0156708 A1 | 6/2009 | Lai et al. |
| 2010/0041822 A1 | 2/2010 | Hashemzadeh |
| 2011/0028673 A1 | 2/2011 | Fujisawa et al. |

FOREIGN PATENT DOCUMENTS

| | | |
|---|---|---|
| EP | 0 753 521 | 1/1997 |
| EP | 0 965 593 | 12/1999 |
| EP | 1123915 A1 | 8/2001 |
| EP | 1 386 924 A1 | 2/2004 |
| EP | 1 403 396 A1 | 3/2004 |
| EP | 1 426 809 A1 | 6/2004 |
| EP | 1424088 A1 | 6/2004 |
| EP | 1424339 A1 | 6/2004 |
| EP | 1 719 776 A1 | 11/2006 |
| EP | 1 749 812 A1 | 2/2007 |
| GB | 1274382 A | 5/1972 |
| GB | 1 364 360 A | 8/1974 |
| JP | 50-014786 B | 5/1975 |
| JP | 52-168545 U | 12/1977 |
| JP | 55-015110 A | 2/1980 |
| JP | 56-22325 | 3/1981 |
| JP | 63216044 A | 9/1988 |
| JP | 63-301919 A | 12/1988 |
| JP | 04-077489 A | 3/1992 |
| JP | 06-032791 A | 2/1994 |
| JP | 08-283342 A | 10/1996 |
| JP | 2000191667 A | 7/2000 |
| JP | 2000191730 A | 7/2000 |
| JP | 2001048939 A | 2/2001 |
| JP | 2004115790 A | 4/2004 |
| JP | 2006036757 A | 2/2006 |
| WO | WO-96/31792 A1 | 10/1996 |
| WO | WO-01/71392 A1 | 9/2001 |
| WO | WO-02/081532 A1 | 10/2002 |
| WO | WO-03/014130 A1 | 2/2003 |
| WO | WO-03/021336 A1 | 3/2003 |
| WO | WO-03/022322 A2 | 3/2003 |
| WO | WO-03/026541 A1 | 4/2003 |
| WO | WO-03/027123 A1 | 4/2003 |
| WO | WO-03/040193 A2 | 5/2003 |
| WO | WO-03/043668 A2 | 5/2003 |
| WO | WO-03/066688 A1 | 8/2003 |
| WO | WO-03/077792 A2 | 9/2003 |
| WO | WO-2005/005368 A1 | 1/2005 |
| WO | WO-2005/005445 A1 | 1/2005 |
| WO | WO-2005/044829 A1 | 5/2005 |
| WO | WO-2005/090364 A1 | 9/2005 |
| WO | WO-2005/115958 A1 | 12/2005 |
| WO | WO-2007/146137 A2 | 12/2007 |
| WO | WO-2008/005398 A2 | 1/2008 |
| WO | WO-2008/066758 A1 | 6/2008 |
| WO | WO-2009/006285 A1 | 1/2009 |

OTHER PUBLICATIONS

Notice of Allowance for U.S. Appl. No. 12/060,536, filed Apr. 1, 2008 (Applicant—Vistakon; Inventors—Fujisawa, et al.) (7 pages).

Non-Final Rejection issued on Mar. 18, 2010 for U.S. Appl. No. 12/060,536, filed Apr. 1, 2008 (Applicant—Vistakon; Inventors—; Fujisawa, et al.) (8 pages).

Issue Notification issued on Feb. 27, 2013 for U.S. Appl. No. 13/300,576, filed Nov. 19, 2011 (Applicant—Vistakon; Inventors—; Fujisawa, et al.) (1 page).

Notice of Allowance issued on Nov. 5, 2012 for U.S. Appl. No. 13/300,576, filed Nov. 19, 2011 (Applicant—Vistakon; Inventors—; Fujisawa, et al.) (7 pages).

Supplemental Response to Office Action filed on Oct. 15, 2012 for U.S. Appl. No. 13/300,576, filed Nov. 19, 2011 (Applicant—Vistakon; Inventors—Fujisawa, et al.) (8 pages).

Response to Office Action filed on Sep. 5, 2012 for U.S. Appl. No. 13/300,576, filed Nov. 19, 2011 (Applicant—Vistakon; Inventors—Fujisawa, et al.) (11 pages).

(56) References Cited

OTHER PUBLICATIONS

Non-Final Rejection issued on Mar. 5, 2012 for U.S. Appl. No. 13/300,576, filed Nov. 19, 2011 (Applicant—Vistakon; Inventors—; Fujisawa, et al.) (8 pages).
Issue Notification issued on Nov. 30, 2011 for U.S. Appl. No. 11/771,999, filed Jun. 9, 2007 (Applicant—Vistakon; Inventors—Fujisawa, et al.) (1 page).
Notice of Allowance issued on Oct. 13, 2011 for U.S. Appl. No. 11/771,999, filed Jun. 9, 2007 (Applicant—Vistakon; Inventors—Fujisawa, et al.) (2 pages).
Amendment after Notice of Allowance filed on Sep. 22, 2011 for U.S. Appl. No. 11/771,999, filed Jun. 9, 2007 (Applicant—Vistakon; Inventors—Fujisawa, et al.) (2 pages).
Notice of Allowance issued on Aug. 19, 2011 for U.S. Appl. No. 11/771,999, filed Jun. 9, 2007 (Applicant—Vistakon; Inventors—Fujisawa, et al.) (5 pages).
Response after Final Office Action filed on Aug. 11, 2011 for U.S. Appl. No. 11/771,999, filed Jun. 9, 2007 (Applicant—Vistakon; Inventors—Fujisawa, et al.) (10 pages).
Final Rejection issued on Apr. 1, 2011 for U.S. Appl. No. 11/771,999, filed Jun. 9, 2007 (Applicant—Vistakon; Inventors—Fujisawa, et al.) (9 pages).
Amendment and Response to Office Action filed on Mar. 15, 2011 for U.S. Appl. No. 11/771,999, filed Jun. 9, 2007 (Applicant—Vistakon; Inventors—Fujisawa, et al.) (22 pages).
Non-Final Rejection issued on Oct. 15, 2010 for U.S. Appl. No. 11/771,999, filed Jun. 9, 2007 (Applicant—Vistakon; Inventors—Fujisawa, et al.) (10 pages).
Request for Continued Examination filed on Sep. 22, 2010 for U.S. Appl. No. 11/771,999, filed Jun. 9, 2007 (Applicant—Vistakon; Inventors—Fujisawa, et al.) (18 pages).
Final Rejection issued on Mar. 24, 2010 for U.S. Appl. No. 11/771,999, filed Jun. 9, 2007 (Applicant—Vistakon; Inventors—Fujisawa, et al.) (14 pages).
Non-Final Rejection issued on Jul. 31, 2009 for U.S. Appl. No. 11/771,999, filed Jun. 9, 2007 (Applicant—Vistakon; Inventors—Fujisawa, et al.) (17 pages).
Examiner Interview Summary Record (PTOL-413) issued on Jun. 29, 2009 for U.S. Appl. No. 11/771,999, filed Jun. 9, 2007 (Applicant—Vistakon; Inventors—Fujisawa, et al.) (4 pages).
Response to Office Action filed on Jun. 12, 2009 for U.S. Appl. No. 11/771,999, filed Jun. 9, 2007 (Applicant—Vistakon; Inventors—Fujisawa, et al.) (15 pages).
Non-Final Rejection issued on Feb. 10, 2009 for U.S. Appl. No. 11/771,999, filed Jun. 9, 2007 (Applicant—Vistakon; Inventors—Fujisawa, et al.) (12 pages).
Non-Final Rejection issued on Feb. 4, 2010 for U.S. Appl. No. 11/681,406, filed Mar. 2, 2007 (Applicant—Vistakon; Inventors—; Nakamura, et al.) (9 pages).
Request for Continued Examination filed on Jan. 6, 2010 for for U.S. Appl. No. 11/681,406, filed Mar. 2, 2007 (Applicant—Vistakon; Inventors—Nakamura, et al.) (17 pages).
Examiner Interview Summary Record (PTOL-413) issued on Jul. 6, 2009 for U.S. Appl. No. 11/681,406, filed Mar. 2, 2007 (Applicant—Vistakon; Inventors—Nakamura, et al.) (3 pages).
Final Rejection issued on Jul. 6, 2009 for U.S. Appl. No. 11/681,406, filed Mar. 2, 2007 (Applicant—Vistakon; Inventors—; Nakamura, et al.) (10 pages).
Response to Office Action filed on Mar. 13, 2009 for U.S. Appl. No. 11/681,406, filed Mar. 2, 2007 (Applicant—Vistakon; Inventors—Nakamura, et al.) (12 pages).
Non-Final Rejection issued on Nov. 13, 2008 for U.S. Appl. No. 11/681,406, filed Mar. 2, 2007 (Applicant—Vistakon; Inventors—; Nakamura, et al.) (6 pages).
Response to Office Action filed on Jul. 25, 2008 for U.S. Appl. No. 11/681,406, filed Mar. 2, 2007 (Applicant—Vistakon; Inventors—Nakamura, et al.) (34 pages).
Non-Final Rejection issued on Apr. 16, 2008 for U.S. Appl. No. 11/681,406, filed Mar. 2, 2007 (Applicant—Vistakon; Inventors—; Nakamura, et al.) (8 pages).

Response to Office Action filed on Feb. 5, 2008 for U.S. Appl. No. 11/681,406, filed Mar. 2, 2007 (Applicant—Vistakon; Inventors—Nakamura, et al.) (15 pages).
Non-Final Rejection issued on Sep. 14, 2007 for U.S. Appl. No. 11/681,406, filed Mar. 2, 2007 (Applicant—Vistakon; Inventors—; Nakamura, et al.) (6 pages).
Final Rejection filed on Jun. 7, 2012 for U.S. Appl. No. 11/561,525, filed Nov. 20, 2006 (Applicant—Vistakon; Inventors—Fujisawa, et al) (10 pages).
Response to Non-Final Rejection filed on Mar. 28, 2012 for U.S. Appl. No. 11/561,525, filed Nov. 20, 2006 (Applicant—Vistakon; Inventors—Fujisawa, et al) (11 pages).
Non-Final Rejection issued on Sep. 29, 2011 for U.S. Appl. No. 11/561,525, filed Nov. 20, 2006 (Applicant—Vistakon; Inventors—Fujisawa, et al) (10 pages).
Response to Non-Final Rejection filed Jul. 5, 2011 for U.S. Appl. No. 11/561,525, filed Nov. 20, 2006 (Applicant—Vistakon; Inventors—Fujisawa, et al) (10 pages).
Non-Final Rejection issued on Jan. 4, 2011 for U.S. Appl. No. 11/561,525, filed Nov. 20, 2006 (Applicant—Vistakon; Inventors—Fujisawa, et al) (6 pages).
Request for Continued Examination filed on Nov. 24, 2010 for U.S. Appl. No. 11/561,525, filed Nov. 20, 2006 (Applicant—Vistakon; Inventors—Fujisawa, et al) (14 pages).
Final Rejection issued on May 24, 2010 for U.S. Appl. No. 11/561,525, filed Nov. 20, 2006 (Applicant—Vistakon; Inventors—Fujisawa, et al) (8 pages).
Response to Non-Final Rejection filed on Feb. 16, 2010 for U.S. Appl. No. 11/561,525, filed Nov. 20, 2006 (Applicant—Vistakon; Inventors—Fujisawa, et al) (13 pages).
Non-Final Rejection issued on Sep. 14, 2009 U.S. Appl. No. 11/561,525, filed Nov. 20, 2006 (Applicant—Vistakon; Inventors—Fujisawa, et al) (11 pages).
Examiner Interview Summary Record issued on Jul. 31, 2009 for U.S. Appl. No. 11/561,525, filed Nov. 20, 2006 (Applicant—Vistakon; Inventors—Fujisawa, et al) (4 pages).
Response to Non-Final Rejection filed on Mar. 30, 2009 for U.S. Appl. No. 11/561,525, filed Nov. 20, 2006 (Applicant—Vistakon; Inventors—Fujisawa, et al) (5 pages).
Non-Final Rejection issued on Oct. 30, 2008 for U.S. Appl. No. 11/561,525, filed Nov. 20, 2006 (Applicant—Vistakon; Inventors—Fujisawa, et al) (10 pages).
Response to Non-Final Rejection filed on Aug. 5, 2008 for U.S. Appl. No. 11/561,525, filed Nov. 20, 2006 (Applicant—Vistakon; Inventors—Fujisawa, et al) (28 pages).
Non-Final Rejection issued on Apr. 8, 2008 for U.S. Appl. No. 11/561,525, filed Nov. 20, 2006 (Applicant—Vistakon; Inventors—Fujisawa, et al) (13 pages).
Non-Final Rejection issued on Jun. 27, 2013 for U.S. Appl. No. 13/746,268, filed Jan. 21, 2013 (Applicant—Vistakon; Inventor—Fujisawa) (5 pages).
Issue Notification issued on Dec. 29, 2012 for U.S. Appl. No. 12/901,191, filed Oct. 8, 2010 (Applicant—; Vistakon; Inventor—Fujisawa) (1 page).
Notice of Allowance issued on Sep. 4, 2012 for U.S. Appl. No. 12/901,191, filed Oct. 8, 2010 (Applicant—; Vistakon; Inventor—Fujisawa) (5 pages).
Response to Non-Final Rejection filed on Jun. 20, 2012 for U.S. Appl. No. 12/901,191, filed Oct. 8, 2010 (Applicant—; Vistakon; Inventor—Fujisawa)(26 pages).
Non-Final Rejection issued on Dec. 20, 2011 for U.S. Appl. No. 12/901,191, filed Oct. 8, 2010 (Applicant—; Vistakon; Inventor—Fujisawa)) (5 pages).
Response to Election/Restriction Requirement filed on Oct. 27, 2011 for U.S. Appl. No. 12/901,191, filed Oct. 8, 2010 (Applicant—; Vistakon; Inventor—Fujisawa) (16 pages).
Requirement for Restriction/Election issued on Apr. 27, 2011 for ; U.S. Appl. No. 12/901,191, filed Oct. 8, 2010 (Applicant—; Vistakon; Inventor—Fujisawa) (10 pages).
Issue Notification issued on Nov. 3, 2010 for U.S. Appl. No. 11/561,456, filed Nov. 20, 2006 (Applicant—Vistakon; Inventor—; Fujisawa) (1 page).

(56) References Cited

OTHER PUBLICATIONS

Notice of Allowance issued on Jul. 8, 2010 for U.S. Appl. No. 11/561,456, filed Nov. 20, 2006 (Applicant—Vistakon; Inventor—; Fujisawa) (6 pages).
Response After Final Action filed on Jun. 28, 2010 for U.S. Appl. No. 11/561,456, filed Nov. 20, 2006 (Applicant—Vistakon; Inventor—Fujisawa) (14 pages).
Examiner Interview Summary Record issued on May 26, 2010 ; for U.S. Appl. No. 11/561,456, filed Nov. 20, 2006 (Applicant—; Vistakon; Inventor—Fujisawa) (3 pages).
Final Rejection issued on May 6, 2010 for U.S. Appl. No. 11/561,456, filed Nov. 20, 2006 (Applicant—Vistakon; Inventor—; Fujisawa) (6 pages).
Response to Non-Final Rejection filed on Feb. 24, 2010 for U.S. Appl. No. 11/561,456, filed Nov. 20, 2006 (Applicant—Vistakon; ; Inventor—Fujisawa); (23 pages).
Non-Final Rejection issued on Oct. 27, 2009 for U.S. Appl. No. 11/561,456, filed Nov. 20, 2006 (Applicant—Vistakon; Inventor—Fujisawa) (10 pages).
Response to Election/Restriction Requirement filed on Aug. 11, 2009 for U.S. Appl. No. 11/561,456, filed Nov. 20, 2006 (Applicant—Vistakon; Inventor—Fujisawa) (15 pages).
Requirement for Restriction/Election issued on Jun. 11, 2009 for; U.S. Appl. No. 11/561,456, filed Nov. 20, 2006 (Applicant—; Vistakon; Inventor—Fujisawa) (11 pages).
Notice of Allowance issued on Jun. 24, 2013 for U.S. Appl. No. 11/609,724, filed Dec. 12, 2006 (Applicant—Vistakon; Inventors—Nakamura, et al.) (8 pages).
Request for Continued Examination filed on Sep. 28, 2011 for U.S. Appl. No. 11/609,724, filed Dec. 12, 2006 (Applicant—Vistakon; Inventors—Nakamura, et al.) (10 pages).
Final Rejection issued on Mar. 29, 2011 for U.S. Appl. No. 11/609,724, filed Dec. 12, 2006 (Applicant—Vistakon; Inventors—Nakamura, et al.) (7 pages).
Non-Final Rejection issued on Sep. 2, 2010 for U.S. Appl. No. 11/609,724, filed Dec. 12, 2006 (Applicant—Vistakon; Inventors—Nakamura, et al.) (9 pages).
Request for Continued Examination filed on Apr. 15, 2010 ffor U.S. Appl. No. 11/609,724, filed Dec. 12, 2006 (Applicant—Vistakon; Inventors—Nakamura, et al.) (18 pages).
Examiner Interview Summary Record (PTOL-413) issued on Nov. 9, 2009 for U.S. Appl. No. 11/609,724, filed Dec. 12, 2006 (Applicant—Vistakon; Inventors—Nakamura, et al.) (2 pages).
Final Rejection issued on Nov. 9, 2009 for U.S. Appl. No. 11/609,724, filed Dec. 12, 2006 (Applicant—Vistakon; Inventors—Nakamura, et al.) (6 pages).
Response to Office Action filed on Aug. 18, 2009 for U.S. Appl. No. 11/609,724, filed Dec. 12, 2006 (Applicant—Vistakon; Inventors—Nakamura, et al.) (16 pages).
Non-Final Rejection issued on Mar. 27, 2009 for U.S. Appl. No. 11/609,724, filed Dec. 12, 2006 (Applicant—Vistakon; Inventors—Nakamura, et al.) (7 pages).
Response to Office Action filed on Jan. 22, 2009 for U.S. Appl. No. 11/609,724, filed Dec. 12, 2006 (Applicant—Vistakon; Inventors—Nakamura, et al.) (19 pages).
Non-Final Rejection issued on Jul. 22, 2008 for U.S. Appl. No. 11/609,724, filed Dec. 12, 2006 (Applicant—Vistakon; Inventors—Nakamura, et al.) (7 pages).
Election Under Restriction Requirement issued on Jun. 12, 2008 for U.S. Appl. No. 11/609,724, filed Dec. 12, 2006 (Applicant—Vistakon; Inventors—Nakamura, et al.) (11 pages).
Requirement for Restriction/Election issued on Mar. 17, 2008 for U.S. Appl. No. 11/609,724, filed Dec. 12, 2006 (Applicant—Vistakon; Inventors—Nakamura, et al.) (9 pages).
Response to Amendment issued on Oct. 19, 2011 for U.S. Appl. No. 11/609,977, filed Dec. 12, 2006 (Applicant—Vistakon; Inventors—Nakamura, et al) (2 pages).
Amendment after Notice of Allowance filed with the USPTO ; on Oct. 19, 2011 for U.S. Appl. No. 11/609,977, filed Dec. 12, 2006 (Applicant—Vistakon; Inventors—Nakamura, et al) (2 pages).
Issue Notification issued on Oct. 19, 2011for U.S. Appl. No. 11/609,977, filed Dec. 12, 2006 (Applicant—Vistakon; Inventors—Nakamura, et al) (1 page).
Amendment after Notice of Allowance filed with the USPTO ; on Sep. 22, 2011 for U.S. Appl. No. 11/609,977, filed Dec. 12, 2006 (Applicant—Vistakon; Inventors—Nakamura, et al) (2 pages).
Request for Continued Examination filed with the USPTO ; on Aug. 16, 2010 for U.S. Appl. No. 11/609,677, filed Dec. 12, 2006 ; (Applicant—Vistakon; Inventors—Nakamura, et al) (14 pages).
Response to Office Action filed with the USPTO on Nov. 11, 2009 ; for U.S. Appl. No. 11/609,977, filed Dec. 12, 2006 (Applicant—Vistakon; Inventors—Nakamura, et al)(10 pages).
International Preliminary Report issued on Jun. 29, 2010 for ; PCT/US2008/088287 filed on Dec. 24, 2008 and published as WO 2009/086444 on Jul. 9, 2009 (Applicant—Johnson & Johnson Vision Care, Inc.; Inventors—Fujisawa, et al.) (7 pages).
Written Opinion mailed on Apr. 28, 2009 for ; PCT/US2008/088287 filed on Dec. 24, 2008 and published as WO 2009/086444 on Jul. 9, 2009 (Applicant—Johnson & Johnson Vision Care, Inc.; Inventors—Fujisawa, et al.) (6 pages).
International Search Report mailed on Apr. 28, 2009 for ; PCT/US2008/088287 filed on Dec. 24, 2008 and published as WO 2009/086444 on Jul. 9, 2009 (Applicant—Johnson & Johnson Vision Care, Inc.; Inventors—Fujisawa, et al.) (3 pages).
Written Opinion mailed on Sep. 23, 2008 for ; PCT/US2008/068544 filed on Jun. 27, 2008 and published as WO 2009/006285 on Jan. 8, 2009 (Applicant—Johnson & Johnson Vision Care, Inc.; Inventors—Fujisawa, et al.) (5 pages).
International Search Report mailed on Sep. 23, 2008 for ; PCT/US2008/068544 filed on Jun. 27, 2008 and published as WO 2009/006285 on Jan. 8, 2009 (Applicant—Johnson & Johnson Vision Care, Inc.; Inventors—Fujisawa, et al.) (1 page).
Written Opinion mailed on Apr. 24, 2008 for PCT/US2007/024325 ; filed on Nov. 20, 2007 and published as WO 2008/066758 on Jun. 5, 2008 (Applicant—Johnson & Johnson Vision Care, Inc.; Inventors—Nakamura, et al.) (6 pages).
International Preliminary Report on Patentability issued on ; May 26, 2009 for PCT/US2007/024325 filed on Nov. 20, 2007 and published as WO 2008/066758 on Jun. 5, 2008 (Applicant—Johnson & Johnson Vision Care, Inc.; Inventors—Nakamura, et al.) (1 page).
Written Opinion mailed on Jan. 25, 2008 for PCT/US2007/020668 ; filed on Sep. 25, 2007 and published as WO 2008/042158 on Apr. 10, 2008 (Applicant—Johnson & Johnson Vision Care, Inc.; Inventors—Fujisawa, et al.) (7 pages).
International Preliminary Report on Patentability issued on ; Mar. 31, 2009 for PCT/US2007/020668 field on Sep. 25, 2007 and published as WO 2008/042158 on Apr. 10, 2008 (Applicant—Johnson & Johnson Vision Care, Inc.; Inventors—Fujisawa, et al.) (1 page).
Written Opinion mailed on Jan. 25, 2008 for PCT/US2007/020683 ; filed on Sep. 25, 2007 and published as WO 2008/042163 on Apr. 10, 2008 (Applicant—Johnson & Johnson Vision Care, Inc.; Inventors—Fujisawa, et al.) (5 pages).
International Preliminary Report on Patentabiilty issued on ; Mar. 31, 2009 for PCT/US2007/020683 filed on Sep. 25, 2007 and published as WO 2008/042163 on Apr. 10, 2008 (Applicant—Johnson & Johnson Vision Care, Inc.; Inventors—Fujisawa, et al.) (6 pages).
International Preliminary Report on Patentability issued on Jun. 16, 2009 for PCT/US2007/015150 filed on Jun. 28, 2007 and published as WO 2008/0147374 on Dec. 4, 2008 (Applicant—Johnson & Johnson Vision Care, Inc.; Inventors—Nakamura, et al.) (6 pages).
Written Opinion mailed on Jun. 9, 2009 for PCT/US2007/015150 ; filed on Jun. 28, 2007 and published as WO 2008/0147374 on Dec. 4, 2008 (Applicant—Johnson & Johnson Vision Care, Inc.; Inventors—Nakamura, et al.) (5 pages).
International Search Report mailed on Jun. 9, 2009 for ; PCT/US2007/015150 field on Jun. 28, 2007 and published as WO 2008/0147374 on Dec. 4, 2008 (Applicant—Johnson & Johnson Vision Care, Inc.; Inventors—Nakamura, et al.) (4 pages).
International Preliminary Report on Patentabiilty issued on Jul. 17, 2007 ; for PCT/SE2006/000023 filed on Sep. 1, 2006 and published ; as WO 2006/075948 on Jul. 20, 2006 (Applicant—Molnlycke Health; Care AB; Inventors—Fabo, et al.).

(56) References Cited

OTHER PUBLICATIONS

International Search Report issued by the International Bureau on ; Apr. 27, 2006 for PCT/SE2006/000023 filed on Sep. 1, 2006 and published ; as WO 2006/075948 on Jul. 20, 2006 (Applicant—Molnlycke Health; Care AB; Inventors—Fabo, et al.).
Written Opinion issued by the International Bureau on ; Apr. 27, 2006 for PCT/SE2006/000023 filed on Sep. 1, 2006 and published ; as WO 2006/075948 on Jul. 20, 2006 (Applicant—Molnlycke Health; Care AB; Inventors—Fabo, et al.).
Adams, et al. (2000) Metal Segregation in Bimetallic Clusters and Its Possible; Role in Synergism and Bifunctional Catalysis. Journal of Organometallic ; Chemistry, 600: 1-6.
Fortuniak, et al. (2001) Controlled Synthesis of Siloxan Polymers and Siloxan-; Siloxane Block Copolymers with 3-Chloropropyl Groups Pendat to the Siloxane; Chain. Macomol. Chem. Phys., 202: 2306-2313.
Gaylord. Composition for Manufacturing Contact Lenses. Accession No. 1976: 578430, based on Brazilian Patent No. 7403534.
Hirabayashi, et al. (1998) A facile preparation and cyclopropanation of 1-alkenylsilanols. Bulletin of the Chemical Society of Japan, 71(10: 2409-2417.
HQMME Product Literature, Eastman Chemicals website, http://www.eastman.;Com/Literature_Center/D/D162.pdf, last accessed (Jun. 29, 2009).
Hurd, et al. (1955) On the Mechanism of the Acid-catalyzed Rearrangement of Siloxane Linkages in Organopolysiloxanes. Journal of the American Chemistry Society, 77: 2998-3001.
Kawakami, et al. (1996) Synthesis and characterization of liquid crystalline polystyrenes with disiloxane linkage int he spacer. Polymer Bulletin (Berlin), 36(6): 653-658.
Kunzler. (1996) Silicone Hydrogels for Contact Lens Application. Trends in Polymer Science, 4:2): 52-59.
Lai, et al. (1995) Role of Bulky Polysiloxanylalkyl Methacrylates in Oxygen-Permeable Hydrogel Materials. Jounral of Applied Polymer Science, 56(3): 317-324.
Material Safety Data Sheet of 2-Ethylhexyl acrylate, Japan Petrochemical ; Industry Association, May 25, 1986 (revised in Aug. 2001), p. 4-5, Item 1-, II.; 1-10, available at http://www.jpca.or.jp/61msds/j7cb32.htm (accessed Jul. 17, 2008).
Plueddemann, et al. (1959) Epoxyorganosilozanes. J. Am. Chem. Soc., 81: ; 2632-2635.
Volkova, et al. (1988) Reaction of dimethylsiloxacyclohexane with methacrylic ; acid and triethylsilanol: Synthesis of [(methacryloyloxy)butyl]dimethyl; (triethylsiloxy)silane. Zhurnal Obshchei Khimii, 58(9): 2145-2148.
Response to Office Action filed on Aug. 9, 2013 for U.S. Appl. No. 12/962,575, filed Dec. 7, 2010 (Applicant—Vistakon; Inventors—Fujisawa, et al.) (14pages).
Amendment after Notice of Allowance filed with the USPTO; on Sep. 22, 2011 for U.S. Appl. No. 11/609,977, filed Dec. 12, 2006 (Applicant—Vistakon; Inventors—Nakamura, et al) (2 pages).
Notice of Allowance issued on Jul. 21, 2011 for U.S. Appl. No. 11/609,977, filed Dec. 12, 2006 (Applicant—Vistakon; Inventors—Nakamura, et al) (12 pages).
Response to Office Action filed with the USPTO on May 3, 2011; for U.S. Appl. No. 11/609,977, filed Dec. 12, 2006 (Applicant—Vistakon; Inventors—Nakamura, et al) (12 pages).
Non-Final Office Action issued on Nov. 9, 2010 for U.S. Appl. No. 11/609,677, filed Dec. 12, 2006 (Applicant—Vistakon; Inventors—Nakamura, et al) (8 pages).
Request for Continued Examination filed with the USPTO; on Aug. 16, 2010 for U.S. Appl. No. 11/609,677, filed Dec. 12, 2006; (Applicant—Vistakon; Inventors—Nakamura, et al) (14 pages).
Final Rejection issued on Mar. 15, 2010 for U.S. Appl. No. 11/609,677, filed Dec. 12, 2006 (Applicant—Vistakon; Inventors—Nakamura, et al) (6 pages).
Response to Office Action filed with the USPTO on Nov. 11, 2009; for U.S. Appl. No. 11/609,977, filed Dec. 12, 2006 (Applicant—Vistakon; Inventors—Nakamura, et al)(10 pages).
Non-Final Office Action issued on May 11, 2009 for U.S. Appl. No. 11/609,677, filed Dec. 12, 2006 (Applicant—Vistakon; Inventors—Nakamura, et al).
International Search Report for PCT/US2007/015264.
International Search Report for PCT/US2007/020668.
International Search Report for PCT/US2007/020683.
International Preliminary Report issued on Jun. 29, 2010 for; PCT/US2008/088287 filed on Dec. 24, 2008 and published as WO 2009/086444 on Jul. 9, 2009 (Applicant—Johnson & Johnson Vision Care, Inc.; Inventors—Fujisawa, et al.) (7 pages).
Written Opinion mailed on Apr. 28, 2009 for; PCT/US2008/088287 filed on Dec. 24, 2008 and published as WO 2009/086444 on Jul. 9, 2009 (Applicant—Johnson & Johnson Vision Care, Inc.; Inventors—Fujisawa, et al.) (6 pages).
International Search Report mailed on Apr. 28, 2009 for; PCT/US2008/088287 filed on Dec. 24, 2008 and published as WO 2009/086444 on Jul. 9, 2009 (Applicant—Johnson & Johnson Vision Care, Inc.; Inventors—Fujisawa, et al.) (3 pages).
Written Opinion mailed on Sep. 23, 2008 for; PCT/US2008/068544 filed on Jun. 27, 2008 and published as WO 2009/006285 on Jan. 8, 2009 (Applicant—Johnson & Johnson Vision Care, Inc.; Inventors—Fujisawa, et al.) (5 pages).
International Preliminary Report on Patentability issued on Jan. 5, 2010 for PCT/US2008/068544 filed on Jun. 27, 2008 and published as WO 2009/006285 on Jan. 8, 2009 (Applicant—Johnson & Johnson Vision Care, Inc.; Inventors—Fujisawa, et al.) (6 pages).
International Search Report mailed on Sep. 23, 2008 for; PCT/US2008/068544 filed on Jun. 27, 2008 and published as WO 2009/006285 on Jan. 8, 2009 (Applicant—Johnson & Johnson Vision Care, Inc.; Inventors—Fujisawa, et al.) (1 page).
Written Opinion mailed on Apr. 24, 2008 for PCT/US2007/024325; filed on Nov. 20, 2007 and published as WO 2008/066758 on Jun. 5, 2008 (Applicant—Johnson & Johnson Vision Care, Inc.; Inventors—Nakamura, et al.) (6 pages).
International Preliminary Report on Patentability issued on; May 26, 2009 for PCT/US2007/024325 filed on Nov. 20, 2007 and published as WO 2008/066758 on Jun. 5, 2008 (Applicant—Johnson & Johnson Vision Care, Inc.; Inventors—Nakamura, et al.) (1 page).
Written Opinion mailed on Jan. 25, 2008 for PCT/US2007/020668; filed on Sep. 25, 2007 and published as WO 2008/042158 on Apr. 10, 2008 (Applicant—Johnson & Johnson Vision Care, Inc.; Inventors—Fujisawa, et al.) (7 pages).
Volkova, et al. (1988) Reaction of dimethylsiloxacyclohexane with methacrylic; acid and triethylsilanol: Synthesis of [(methacryloyloxy)butyl]dimethyl; (triethylsiloxy)silane. Zhurnal Obshchei Khimii, 58(9): 2145-2148.
Response to Office Action filed on Aug. 9, 2013 for U.S. Appl. No. 12/962,575, filed Dec. 7, 2010 (Applicant—Vistakon; Inventors—Fujisawa, et al.) (14 pages).
Non-Final Rejection issued on Apr. 9, 2013 for U.S. Appl. No. 12/962,575, filed Dec. 7, 2010 (Applicant—Vistakon; Inventors—Fujisawa, et al.) (9 pages).
International Search Report for PCT/US2007/024325.
Non-Final Rejection issued on Sep. 12, 2013 for U.S. Appl. No. 13/671,445, filed Nov. 7, 2012 (Applicant—Vistakon; Inventors—Fujisawa, et al.) (6 pages).

* cited by examiner

HYDROLYSIS-RESISTANT SILICONE COMPOUNDS

CROSS-REFERENCE TO RELATED APPLICATIONS

This application is a divisional of U.S. Nonprovisional application Ser. No. 12/901,191, filed Oct. 8, 2010, which application claimed the benefit of U.S. Nonprovisional application Ser. No. 11/561,456, filed Nov. 20, 2006, which application claimed the benefit of U.S. Provisional Application No. 60/848,317, filed Sep. 29, 2006, all of which are hereby incorporated herein by reference in their entireties.

BACKGROUND

As monomers for preparing ophthalmic lenses, monomers having silicon-containing groups are known. For example, 3-[tris(trimethylsiloxy)silyl]propyl methacrylate is widely used as a monomer for preparing ophthalmic lenses. The polymer obtained by copolymerizing 3-[tris(trimethylsiloxy)silyl]propyl methacrylate and N,N-dimethylacrylamide which is a hydrophilic monomer has advantageous features that it is transparent and has a high oxygen permeability. However, if a carboxylic acid such as methacrylic acid is used as a copolymerization component in order to obtain a higher moisture content, the silicone component is gradually hydrolyzed, so that the physical properties of the contact lens may be degraded when the contact lens is stored for a long period.

On the other hand, to improve the hydrolysis resistance, 3-[tris(triethylsiloxy)silyl]propyl methacrylate described in U.S. Pat. No. 3,377,371 was prepared, and hydrolysis test was conducted after adding a carboxylic acid. As a result, although the polymer exhibited a relatively good stability at 80° C., it was proved that it is hydrolyzed at 90° C.

Thus, conventional silicon-containing materials typically fail to provide satisfactory hydrolysis resistance while retaining advantageous transparency and oxygen permeability. Therefore, there remains a need for methods and compositions that overcome these deficiencies and that effectively provide hydrolysis resistant silicon-containing materials.

SUMMARY

As embodied and broadly described herein, the invention, in one aspect, relates to hydrolysis-resistant silicone compounds.

Disclosed are sterically hindered hydrolysis-resistant silicone compounds. For example, the compounds can have a sterically hindered terminal silicon group. As a further example, the compounds can have cyclic siloxane moieties.

Also disclosed are improved purity hydrolysis-resistant silicone compounds. For example, the compounds can be provided having less disiloxane side-product(s).

Also disclosed are processes for making hydrolysis-resistant silicone compounds. In a further aspect, the invention relates to reacting an alkoxysilyl compound with one or more silyl halide compounds. In a yet further aspect, the invention relates to reacting a silyl halide with a silanol. In a yet further aspect, the invention relates to preparing cyclic siloxane monomers.

Also disclosed are the products of the disclosed processes.

Also disclosed are compositions and polymers comprising the disclosed compounds and products of the disclosed processes.

Also disclosed are ophthalmic lenses, for example contact lenses, intraocular lenses, artificial cornea, and spectacle lenses, comprising the disclosed compositions, disclosed polymers, disclosed compounds, and products of the disclosed processes.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

The accompanying drawings, which are incorporated in and constitute a part of this specification, illustrate several embodiments and together with the description illustrate the disclosed compositions and methods.

DETAILED DESCRIPTION

Figure 1:
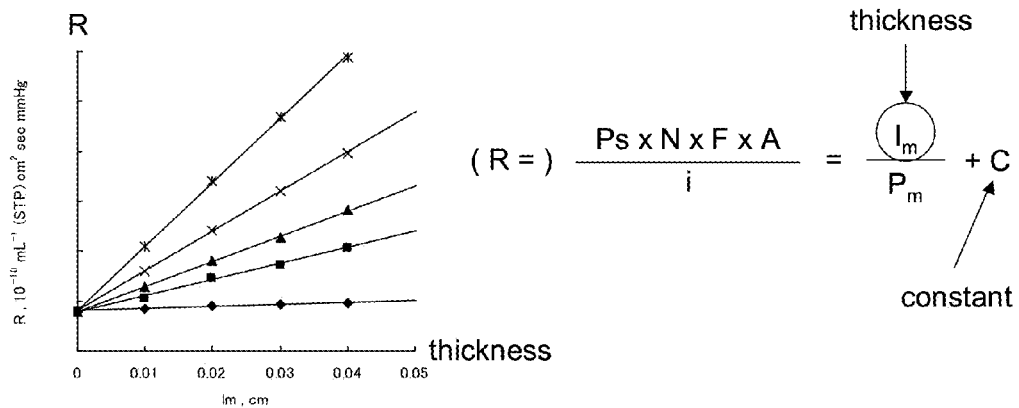
FIG. 1 shows a plot of R (1/Q) versus thickness (lm).

The present invention can be understood more readily by reference to the following detailed description of aspects of the invention and the Examples included therein.

Before the present compounds, compositions, articles, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular embodiments only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which may need to be independently confirmed.

A. DEFINITIONS

As used in the specification and the appended claims, the singular forms "a," "an" and "the" include plural referents unless the context clearly dictates otherwise. Thus, for example, reference to "a component," "a polymer," or "a residue" includes mixtures of two or more such components, polymers, or residues, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the terms "optional" or "optionally" means that the subsequently described event or circumstance may or may not occur, and that the description includes instances where said event or circumstance occurs and instances where it does not.

As used herein, the term "copolymer" refers to a polymer formed from two or more different repeating units (monomer residues). By way of example and without limitation, a copolymer can be an alternating copolymer, a random copolymer, a block copolymer, or a graft copolymer.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, for example, 1 to 12 carbon atoms, or 1 to 6 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, substituted or unsubstituted alkyl, cycloalkyl, alkoxy, amino, ether, halide, hydroxy, nitro, silyl, sulfo-oxo, or thiol, as described herein. A "lower alkyl" group is an alkyl group containing from one to six carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, substituted or unsubstituted alkyl, cycloalkyl, alkoxy, amino, ether, halide, hydroxy, nitro, silyl, sulfo-oxo, or thiol as described herein.

The term "polyalkylene group" as used herein is a group having two or more CH$_2$ groups linked to one another. The polyalkylene group can be represented by the formula —(CH$_2$)$_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or —OA$^1$-(OA$^2$)$_a$-OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $NA^1A^2A^3$, where $A^1$, $A^2$, and $A^3$ can be, independently, hydrogen or substituted or unsubstituted alkyl, cycloalkyl, alkenyl, cycloalkenyl, alkynyl, cycloalkynyl, aryl, or heteroaryl group as described herein.

The term "carboxylic acid" as used herein is represented by the formula —C(O)OH.

The term "ester" as used herein is represented by the formula —OC(O)$A^1$ or —C(O)O$A^1$, where $A^1$ can be a substituted or unsubstituted alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, a substituted or unsubstituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, a substituted or unsubstituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "hydroxyl" as used herein is represented by the formula —OH.

The term "ketone" as used herein is represented by the formula $A^1$C(O)$A^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —Si$A^1A^2A^3$, where $A^1$, $A^2$, and $A^3$ can be, independently, hydrogen or a substituted or unsubstituted alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas $-S(O)A^1$, $-S(O)_2A^1$, $-OS(O)_2A^1$, or $-OS(O)_2OA^1$, where $A^1$ can be hydrogen or a substituted or unsubstituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula $-S(O)_2A^1$, where $A^1$ can be hydrogen or a substituted or unsubstituted alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group as described herein.

The term "thiol" as used herein is represented by the formula $-SH$.

As used herein, the term "siloxanyl" refers to a structure having at least one Si—O—Si bond. Thus, for example, siloxanyl group means a group having at least one Si—O—Si moiety, and siloxanyl compound means a compound having at least one Si—O—Si group.

As used herein, the term "alkoxysilyl" refers to a structure having at least one Si—O-$A^1$ bond. Thus, for example, alkoxysilyl group means a group having at least one Si—O-$A^1$ moiety, and alkoxysilyl compound means a compound having at least one Si—O-$A^1$ group. In a further aspect, alkoxysilyl can have one Si—O-$A^1$ group. In various aspects, $A^1$ of an alkoxysilyl moiety can be a substituted or unsubstituted alkyl, cycloalkyl, alkenyl, cycloalkenyl, alkynyl, cycloalkynyl, aryl, or heteroaryl group as described herein. It is also contemplated that the term alkoxysilyl can, in a further aspect, include substituted alkoxysilyl groups and alkoxysilyl derivatives, including hydrolyzed alkoxysilyl groups (i.e., silanol groups).

As used herein, the term "silyl halide" refers to a structure represented by a formula $X^1SiA^1A^2A^3$ or $X^1X^2SiA^1A^2$ or $X^1X^2X^3SiA^1$ or $X^1X^2X^3X^4Si$, where $X^1$, $X^2$, $X^3$, and $X^4$ are independently fluorine, chlorine, bromine, or iodine, and where $A^1$, $A^2$, and $A^3$ are, independently, hydrogen or a substituted or unsubstituted alkyl, cycloalkyl, alkoxy, alkenyl, cycloalkenyl, alkynyl, cycloalkynyl, aryl, or heteroaryl group as described herein. In a further aspect, silyl halide can have the structure $X^1SiA^1A^2A^3$.

As used herein, the term "silanol" refers to a silyl moiety having a structure represented by the formula $-SiA^1A^2A^3A^4$, where $A^1$, $A^2$, $A^3$, and $A^4$ can be, independently, hydrogen or a substituted or unsubstituted alkyl, cycloalkyl, alkoxy, alkenyl, cycloalkenyl, alkynyl, cycloalkynyl, aryl, or heteroaryl group as described herein, with the proviso that at least one of $A^1$, $A^2$, $A^3$, and $A^4$ is hydroxyl. In a further aspect, one of $A^1$, $A^2$, $A^3$, and $A^4$ is hydroxyl.

As used herein, the terms "silanoxy" and "silanoxyl" refer to a silyl moiety having a structure represented by the formula $-OSiA^1A^2A^3$, where $A^1$, $A^2$, and $A^3$ can be, independently, hydrogen or a substituted or unsubstituted alkyl, cycloalkyl, alkoxy, alkenyl, cycloalkenyl, alkynyl, cycloalkynyl, aryl, or heteroaryl group as described herein.

As used herein, the term "alkylacrylic acid" refers to acrylic acid, alkyl-substituted acrylic acids, salts thereof, and derivatives thereof. In one aspect, an alkylacrylic acid can be further substituted. In a further aspect, an alkylacrylic acid is methacrylic acid.

As used herein, the term "hydrolyzable group" refers to a group or moiety which is convertible to hydrogen by hydrolysis or solvolysis. In one aspect, a hydrolyzable group can be hydrolyzed (i.e., converted to a hydrogen group) by exposure to water or a protic solvent at or near ambient temperature and at or near atmospheric pressure. In further aspects, a hydrolyzable group can be hydrolyzed by exposure to water or a protic solvent at an elevated temperature or an elevated pressure. In further aspects, a hydrolyzable group can be hydrolyzed by exposure to acidic or alkaline water or acidic or alkaline protic solvent.

As used herein, the term "sterically hindered" refers to a tertiary or quaternary substituted moiety wherein at least one of the substituents has at least two carbon atoms. For example, a sterically hindered moiety can have the structure:

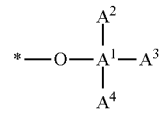

wherein $A^1$ is a carbon atom or silicon atom and wherein at least one of $A^2$, $A^3$, and $A^4$ is an organic group having at least two carbon atoms. In a further aspect, at least one of $A^2$, $A^3$, and $A^4$ is methyl, and at least one of $A^2$, $A^3$, and $A^4$ is an organic group having at least two carbon atoms.

One example of a sterically hindered group is a sterically hindered terminal silicon group, which can have the structure:

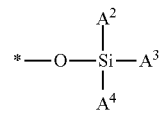

wherein at least one of $A^2$, $A^3$, and $A^4$ is an organic group having at least two carbon atoms. In a further aspect, at least one of $A^2$, $A^3$, and $A^4$ is methyl, and at least one of $A^2$, $A^3$, and $A^4$ is an organic group having at least two carbon atoms.

As used herein, the term "radical-polymerizable group" refers to a moiety that can undergo addition polymerization when exposed to a radical source, for example a radical initiator. Radical polymerizable groups include olefins and acrylates, for example acrylic acid and its derivatives (e.g., alkyl acrylates) and methacrylic acid and its derivatives (e.g., alkyl methacrylates). Such a polymerization typically proceeds through a chain growth mechanism and exhibits chain growth kinetics.

As used herein, the term "hydrolysis resistance" refers to the capacity of a compound or composition to survive hydrolysis conditions. In one aspect, acid hydrolysis is contemplated. As used herein, the term "hydrolysis-resistant" refers to the characteristic of surviving hydrolysis conditions. In one aspect, a residue of a compound can be referred to as hydrolysis-resistant if a composition exhibits greater hydrolysis resistance when comprising the residue of the compound as compared to a similar composition in the absence of the residue of the compound.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C—F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. HYDROLYSIS-RESISTANT SILICONE COMPOUNDS

In one aspect, the invention relates to sterically hindered hydrolysis-resistant silicone compounds. That is, a silicone compound can have at least one sterically hindered terminal silicon group and, thus, having improved resistance to hydrolysis conditions. In a further aspect, the invention relates to improved purity hydrolysis-resistant silicone compounds. That is, a silicone compound can have decreased disiloxane side-product and, thus, improved yield and purity.

1. Sterically Hindered Hydrolysis-Resistant Silicone Compounds

In one aspect, the invention relates to sterically hindered hydrolysis-resistant silicone compounds having the structure:

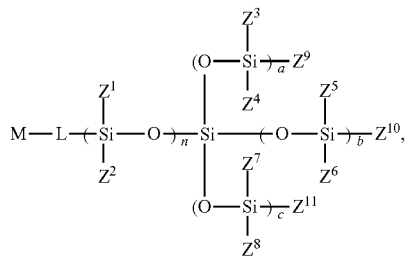

wherein M represents a radical-polymerizable group; wherein L represents an optionally substituted divalent $C_1$-$C_{20}$ organic group; wherein $Z^1$ to $Z^{11}$ independently represent optionally substituted $C_1$-$C_{20}$ alkyl groups or optionally substituted $C_6$-$C_{20}$ aryl groups, with the provisos that: at least one of $Z^3$, $Z^4$, and $Z^9$ is methyl, and at least one of $Z^3$, $Z^4$, and $Z^9$ is an organic group having at least two carbon atoms, at least one of $Z^5$, $Z^6$, and $Z^{10}$ is methyl, and at least one of $Z^5$, $Z^6$, and $Z^{10}$ is an organic group having at least two carbon atoms, and at least one of $Z^7$, $Z^8$, and $Z^{11}$ is methyl, and at least one of $Z^5$, $Z^6$, and $Z^{10}$ is an organic group having at least two carbon atoms; wherein n represents an integer of from 0 to 200; and wherein a, b, and c independently represent integers of from 0 to 20, with the proviso that a, b, and c are not simultaneously 0.

In one aspect, a, b, and c are 1. In a further aspect, n is 0. In a further aspect, n is 0, and all of a, b, and c are 1. In a yet further aspect, a is 0; b and c are 1; and $Z^9$ comprises a methyl group, an ethyl group, a propyl group, a butyl group, or a phenyl group. In a still further aspect, k is 0, and m is from 1 to 3. In an even further aspect, m is 2 or 3, and a, b, and c are independently from 1 to 20, for example, from 1 to 16, from 1 to 12, from 1 to 8, from 1 to 6, from 1 to 4, from 2 to 16, from 2 to 12, from 2 to 8, from 2 to 6, from 2 to 4, or from 4 to 20. In a further aspect, m is 2 or 3; a, b, and c are 1; and n is 0.

For example, a compound can have the structure:

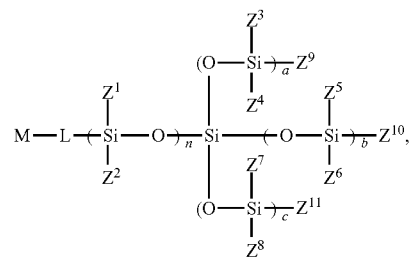

wherein M represents a radical-polymerizable group; wherein L has the structure:

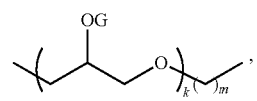

wherein G is hydrogen or a hydrolyzable group; wherein k represents an integer of 0 to 6, and wherein m represents an integer of 1 to 3 when k is 0, and represents an integer of 1 to 20 when k is not 0, with the proviso that 1<3k+m<20; wherein $Z^1$ to $Z^{11}$ independently represent optionally substituted $C_1$-$C_{20}$ alkyl groups or $C_6$-$C_{20}$ aryl groups, with the provisos that: at least one of $Z^3$, $Z^4$, and $Z^9$ is methyl, and at least one of $Z^3$, $Z^4$, and $Z^9$ is an organic group having at least two carbon atoms, at least one of $Z^5$, $Z^6$, and $Z^{10}$ is methyl, and at least one of $Z^5$, $Z^6$, and $Z^{10}$ is an organic group having at least two carbon atoms, and at least one of $Z^7$, $Z^8$, and $Z^{11}$ is methyl, and at least one of $Z^5$, $Z^6$, and $Z^{10}$ is an organic group having at least two carbon atoms; wherein n represents an integer of from 0 to 200; wherein a, b, and c independently represent integers of from 0 to 20, with the proviso that a, b, and c are not simultaneously 0; and wherein the compound exhibits a hydrolysis resistance of at least about 90% at about 90° C.

In one aspect, the sterically hindered hydrolysis-resistant silicone compounds can be cyclic siloxane monomers and can have the structure:

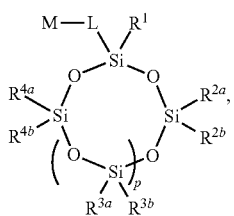

wherein p is 1, 2, or 3; wherein M represents a radical-polymerizable group; wherein L represents an optionally substituted divalent $C_1$-$C_{20}$ organic group; and wherein $R^1$, $R^{2a}$, $R^{2b}$, $R^{3a}$, $R^{3b}$, $R^{4a}$, and $R^{4b}$ independently represent optionally substituted $C_1$-$C_{20}$ alkyl groups or optionally substituted $C_6$-$C_{20}$ aryl groups.

a. Radical-Polymerizable Groups

In one aspect, the sterically hindered hydrolysis-resistant silicone compounds of the invention bear at least one radical-polymerizable group, M. In one aspect, M is any moiety known to those of skill in the art that can undergo addition polymerization when exposed to a radical source, for example a radical initiator. In a further aspect, M can be an olefin. For example, M can be an alkene group, including an ethylene, a 1,3-butadiene moiety, or a styryl moiety. In a further aspect, M can be an acrylate. For example, M can be a residue of acrylic acid or a derivative thereof (e.g., alkyl acrylates) or residue of methacrylic acid or a derivative thereof (e.g., alkyl methacrylates). Specifically, in one aspect, M can be an acryloyloxy group or a methacryloyloxy group.

In a further aspect, M can be an acryloyloxy group, a methacryloyloxy group, acrylamide group, methacrylamide group, N-vinylamide group, or styryl group.

It is understood that one radical-polymerizable group can undergo a polymerization reaction with other radical-polymerizable groups of other compounds of the invention or with radical-polymerizable groups of comonomers, thereby producing a polymer comprising a residue of a compound of the invention.

b. Linking Groups

In one aspect, the sterically hindered hydrolysis-resistant silicone compounds of the invention optionally bear at least one linking group, L. In one aspect, L can be an optionally substituted divalent $C_1$-$C_{20}$ organic group, for example, a substituted or unsubstituted $C_1$-$C_{16}$ organic group, $C_1$-$C_{12}$ organic group, $C_1$-$C_8$ organic group, or a $C_1$-$C_4$ organic group. In a further aspect, linking group, L, can be a substituted or unsubstituted polyalkylene group. That is, L can be a group having two or more $CH_2$ groups linked to one another, represented by the formula $-(CH_2)_a-$, where "a" is an integer of from 1 to 20. Examples include methylene, ethylene, propylene, butylene, pentylene, and hexylene. The organic group can be branched or linear.

In a further aspect, linking group, L, can be substituted by one or more functionalized groups. For example, L can be substituted by hydroxy groups, hydroxyalkyl groups, amino groups, aminoalkyl groups, amide groups, alkylamide groups, alkoxy groups, alkoxyalkyl groups, alkoxycarbonyl groups, alkoxycabonylalkyl groups or a combination of those functionalized groups. In a yet further aspect, L can be substituted by hydroxy groups or hydroxyalkyl groups. Specifically, in one aspect, L can be substituted by hydroxy groups.

In a further aspect, one or more $CH_2$ groups of linking group, L, can be replaced by one or more hetero atoms. For example, one or more $CH_2$ groups of L can be replaced by O, S, $N-R^L$, $P-R^L$ or a combination of those hetero atoms, wherein $R^L$ is substituted or unsubstituted $C_1$-$C_{20}$ alkyl groups or substituted or unsubstituted $C_6$-$C_{20}$ aryl groups and $R^L$ can be substituted by one or more functionalized groups and $CH_2$ groups of $R^L$ can be replaced by one or more hetero atoms. In a yet further aspect, one or more $CH_2$ groups of L can be replaced by O or $N-R^L$.

In a further aspect, L has the structure:

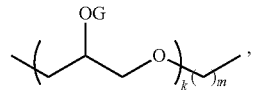

wherein G is hydrogen or a hydrolyzable group; wherein k represents an integer of 0 to 6; and wherein m represents an integer of 1 to 3 when k is 0, and represents an integer of from 1 to 20 when k is not 0, with the proviso that $1<3k+m<20$.

In a further aspect, k is 1, and wherein m is from 1 to 7. In a yet further aspect, L is absent from the compounds and/or compositions of the invention.

c. Siloxanyl Chains

In one aspect, the sterically hindered hydrolysis-resistant silicone compounds of the invention can optionally bear siloxanyl chains having a general structure:

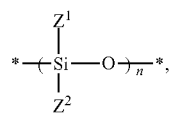

wherein $Z^1$ and $Z^2$ are, independently, substituted or unsubstituted $C_1$-$C_{20}$ alkyl groups or substituted or unsubstituted $C_6$-$C_{20}$ aryl groups.

The $C_1$-$C_{20}$ alkyl groups can be, for example, $C_1$-$C_{16}$ alkyl groups, $C_1$-$C_{12}$ alkyl groups, $C_1$-$C_8$ alkyl groups, $C_1$-$C_6$ alkyl groups, or $C_1$-$C_4$ alkyl groups. Examples include methyl, ethyl, n-propyl, i-propyl, n-butyl, s-butyl, i-butyl, t-butyl, n-pentyl, i-pentyl, s-pentyl, neopentyl, hexyl, heptyl, octyl, decyl, and dodecyl. The alkyl groups can be branched or linear.

The $C_6$-$C_{20}$ aryl groups can be, for example, $C_6$-$C_{20}$ aryl groups, $C_6$-$C_{12}$ aryl groups, or $C_6$-$C_{10}$ aryl groups. Examples include phenyl, toluenyl, pyridinyl, and naphthalenyl.

n can be from 0 to 200, for example, from 0 to 100, from 0 to 50, from 0 to 25, from 0 to 12, from 0 to 10, from 0 to 6, from 0 to 4, from 1 to 200, from 1 to 100, from 1 to 50, from 1 to 25, from 1 to 12, from 1 to 10, from 1 to 6, or from 1 to 4. It is understood that, in a polymer, the average for n can be a non-integer.

In a further aspect, the compounds of the invention can optionally bear siloxanyl chains having a general structure:

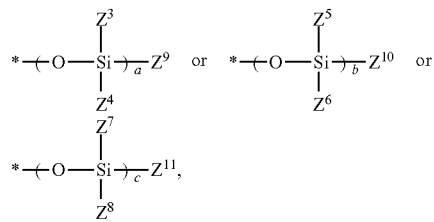

wherein $Z^3$ to $Z^{11}$ independently represent optionally substituted $C_1$-$C_{20}$ alkyl groups or optionally substituted $C_6$-$C_{20}$ aryl groups, with the provisos that: at least one of $Z^3$, $Z^4$, and $Z^9$ is methyl, and at least one of $Z^3$, $Z^4$, and $Z^9$ is an organic group having at least two carbon atoms, at least one of $Z^5$, $Z^6$, and $Z^{10}$ is methyl, and at least one of $Z^5$, $Z^6$, and $Z^{10}$ is an organic group having at least two carbon atoms, and at least one of $Z^7$, $Z^8$, and $Z^{11}$ is methyl, and at least one of $Z^5$, $Z^6$, and $Z^{10}$ is an organic group having at least two carbon atoms.

The $C_1$-$C_{20}$ alkyl groups can be, for example, $C_1$-$C_{16}$ alkyl groups, $C_1$-$C_{12}$ alkyl groups, $C_1$-$C_8$ alkyl groups, $C_1$-$C_6$ alkyl groups, or $C_1$-$C_4$ alkyl groups. Examples include methyl, ethyl, n-propyl, i-propyl, n-butyl, s-butyl, i-butyl, t-butyl, n-pentyl, i-pentyl, s-pentyl, neopentyl, hexyl, heptyl, octyl, decyl, and dodecyl. The alkyl groups can be branched or linear.

For example, each siloxanyl chain can, independently, have a structure represented by the formula:

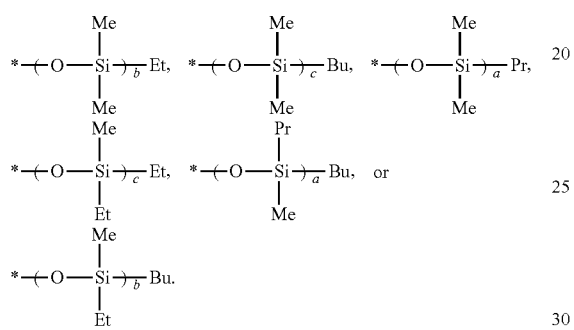

The $C_6$-$C_{20}$ aryl groups can be, for example, $C_6$-$C_{20}$ aryl groups, $C_6$-$C_{12}$ aryl groups, or $C_6$-$C_{10}$ aryl groups. Examples include phenyl, toluenyl, pyridinyl, and naphthalenyl.

For example, each siloxanyl chain can, independently, have a structure represented by the formula:

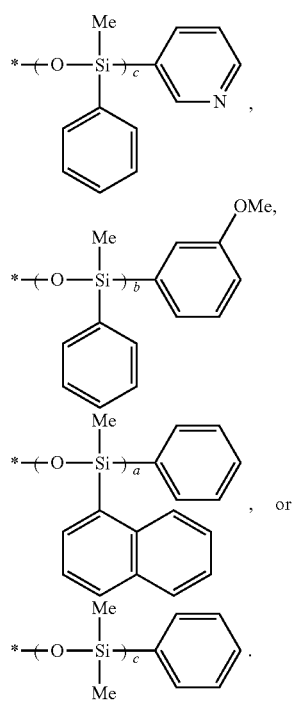

In a further aspect, each of a, b, and c can be an integers of from 0 to 20, for example, from 0 to 12, from 0 to 10, from 0 to 8, from 0 to 6, from 0 to 4, from 1 to 20, from 0 to 12, from 0 to 10, from 0 to 8, from 0 to 6, from 0 to 4, or from 1 to 20, including 1, 2, 3, 4, 5, 6, 7, 8, 9, 10, 11, 12, 13, 14, 15, 16, 17, 18, 19, and 20. It is understood that, in a polymer, the average for any of a, b, and c can be a non-integer. Each of a, b, and c can be the same as or different from the others of a, b, and c.

In a further aspect, two of $Z^3$, $Z^4$, and $Z^9$ are methyl, and one of $Z^3$, $Z^4$, and $Z^9$ is ethyl, propyl, or butyl; wherein two of $Z^5$, $Z^6$, and $Z^{10}$ are methyl, and one of $Z^5$, $Z^6$, and $Z^{10}$ is ethyl, propyl, or butyl; and two of $Z^7$, $Z^8$, and $Z^{11}$ are methyl, and one of $Z^5$, $Z^6$, and $Z^{10}$ is ethyl, propyl, or butyl. In a yet further aspect, $Z^3$, $Z^4$, $Z^5$, $Z^6$, $Z^7$, and $Z^8$ are methyl, and wherein and $Z^9$, $Z^{10}$, and $Z^{11}$ are independently ethyl, propyl, or butyl.

d. Illustrative Structures

As examples, the sterically hindered hydrolysis-resistant silicone compounds of the invention can have a structure represented by the formula:

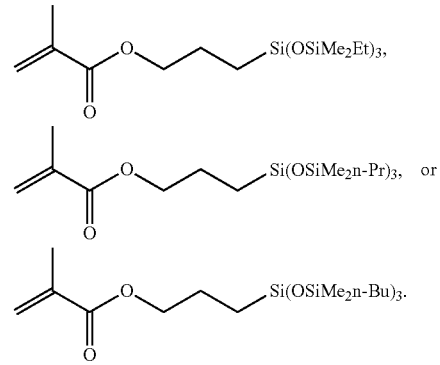

2. Improved Purity Hydrolysis-Resistant Silicone Compounds

In one aspect, the invention relates to improved purity hydrolysis-resistant silicone compounds having the structure:

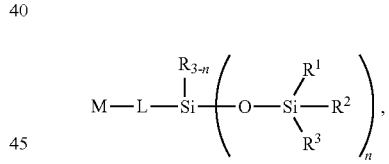

wherein M represents a radical-polymerizable group; wherein L represents an optionally substituted divalent $C_1$-$C_{20}$ organic group; wherein R, $R^1$, $R^2$, and $R^3$ independently represent optionally substituted $C_1$-$C_{20}$ alkyl groups or optionally substituted $C_6$-$C_{20}$ aryl groups, with the proviso that at least one of $R^1$, $R^2$, and $R^3$ is a group having at least 2 carbon atoms; and wherein n represents an integer of from 1 to 3. In certain aspects, n is 1, n is 2, and n is 3.

Such improved purity hydrolysis-resistant silicone compounds compound can be prepared, for example, by the step of reacting a silyl halide having the structure:

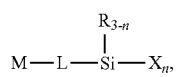

wherein X represents a halogen selected from the group consisting of chlorine, bromine, and iodine, with a silanol having the structure:

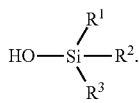

In a further aspect, such a compound can be produced in a yield of at least about 10% by gas chromatography analysis. For example, the yield can be at least about 15%, at least about 20%, at least about 25%, at least about 30%, at least about 35%, at least about 40%, at least about 45%, or at least about 50% by gas chromatography analysis.

In a further aspect, k is 0, and m is from 1 to 3. In a yet further aspect, k is 1, and m is from 1 to 7. In a still further aspect, one of $R^1$, $R^2$, and $R^3$ is methyl, and at least one of $R^1$, $R^2$, and $R^3$ is ethyl, propyl, or butyl. In an even further aspect, two of $R^1$, $R^2$, and $R^3$ are methyl, and one of $R^1$, $R^2$, and $R^3$ is ethyl, propyl, or butyl.

In one aspect, water is substantially absent.

a. Radical-Polymerizable Groups

In one aspect, the improved purity hydrolysis-resistant silicone compounds of the invention bear at least one radical-polymerizable group, M, as disclosed herein. It is also understood that one radical-polymerizable group can undergo a polymerization reaction with other radical-polymerizable groups of other compounds of the invention or with radical-polymerizable groups of comonomers, thereby producing a polymer comprising a residue of a compound of the invention.

b. Linking Groups

In one aspect, the improved purity hydrolysis-resistant silicone compounds of the invention optionally bear at least one linking group, L, as disclosed herein. In a further aspect, L has the structure:

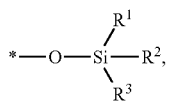

wherein k represents an integer of from 0 to 6; and wherein m represents an integer of from 1 to 3 when k is 0, and represents an integer of from 1 to 20 when k is not 0, with the proviso that $1 \leq 3k+m \leq 20$. In a further aspect, k is 1, and wherein m is from 1 to 7. In a yet further aspect, L is absent from the compounds and/or compositions of the invention.

c. Silanoxy Groups

In one aspect, the compounds of the invention can bear one, two, or three silanoxy groups having a general structure:

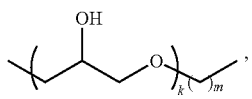

wherein R, $R^1$, $R^2$, and $R^3$ independently represent substituted or unsubstituted $C_1$-$C_{20}$ alkyl groups or substituted or unsubstituted $C_6$-$C_{20}$ aryl groups.

The $C_1$-$C_{20}$ alkyl groups can be, for example, $C_1$-$C_{16}$ alkyl groups, $C_1$-$C_{12}$ alkyl groups, $C_1$-$C_8$ alkyl groups, $C_1$-$C_6$ alkyl groups, or $C_1$-$C_4$ alkyl groups. Examples include methyl, ethyl, n-propyl, i-propyl, n-butyl, s-butyl, i-butyl, t-butyl, n-pentyl, i-pentyl, s-pentyl, neopentyl, hexyl, heptyl, octyl, decyl, and dodecyl. The alkyl groups can be branched or linear.

The $C_6$-$C_{20}$ aryl groups can be, for example, $C_6$-$C_{20}$ aryl groups, $C_6$-$C_{12}$ aryl groups, or $C_6$-$C_{10}$ aryl groups. Examples include phenyl, toluenyl, pyridinyl, and naphthalenyl.

In a further aspect, at least one of $R^1$, $R^2$, and $R^3$ is a group having at least 2 carbon atoms. For example, each silanoxy group can, independently, have a structure represented by the formula:

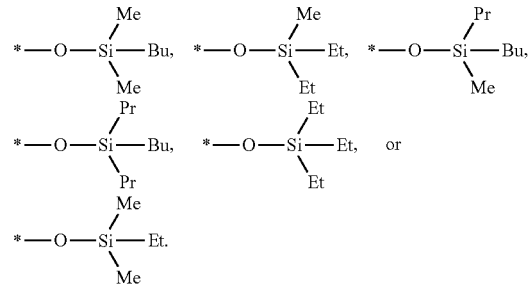

d. Disiloxane Side-Product

In one aspect, a disiloxane compound having the structure:

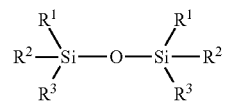

is present in an amount of from about 0% to about 20% by gas chromatography analysis. For example, a disiloxane can be present in an amount of from about 0% to about 15%, from about 0% to about 10%, from about 0% to about 5%, from about 0% to about 3%, from about 0% to about 3%, from about 0% to about 1%, or about 0% by gas chromatography analysis. In one aspect, a disiloxane compound is substantially absent.

C. PROCESSES FOR MAKING HYDROLYSIS-RESISTANT SILICONE COMPOUNDS

In one aspect, the invention relates processes for making sterically hindered hydrolysis-resistant silicone compounds. That is, the processes can make a silicone compound having at least one sterically hindered terminal silicon group and, thus, having improved resistance to hydrolysis conditions. In a further aspect, the invention relates to processes for making improved purity hydrolysis-resistant silicone compounds. That is, the processes can make a silicone compound having decreased disiloxane side-product and, thus, improved yield and purity.

1. Reaction of Alkoxysilyl Compound with Silyl Halide Compound

In one aspect, the invention relates to a process for making a hydrolysis-resistant silicone compound having a sterically-hindered terminal silicon group, the process comprising the step of reacting an alkoxysilyl compound having the structure:

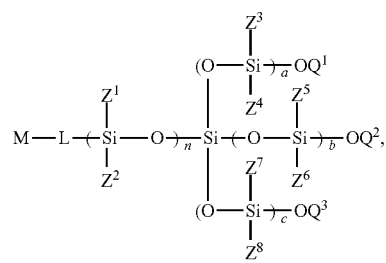

with one or more silyl halide compounds having the structure:

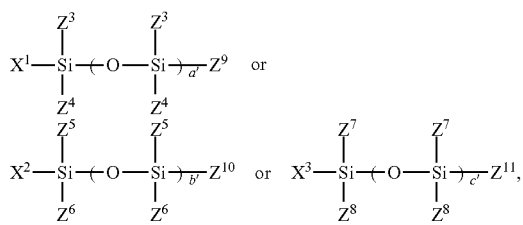

wherein $X^1$, $X^2$, and $X^3$ independently represent a halogen selected from the group consisting of chlorine, bromine, and iodine; wherein M represents a radical-polymerizable group; wherein L represents an optionally substituted divalent $C_1$-$C_{20}$ organic group; wherein n represents an integer of from 0 to 200; wherein $Q^1$, $Q^2$, and $Q^3$ independently represent hydrogen or a hydrolyzable group; wherein $Z^1$ to $Z^{11}$ independently represent optionally substituted $C_1$-$C_{20}$ alkyl groups or optionally substituted $C_6$-$C_{20}$ aryl groups, with the provisos that: at least one of $Z^3$, $Z^4$, and $Z^9$ is methyl, and at least one of $Z^3$, $Z^4$, and $Z^9$ is an organic group having at least two carbon atoms, at least one of $Z^5$, $Z^6$, and $Z^{10}$ is methyl, and at least one of $Z^5$, $Z^6$, and $Z^{10}$ is an organic group having at least two carbon atoms, and at least one of $Z^7$, $Z^8$, and $Z^{11}$ is methyl, and at least one of $Z^5$, $Z^6$, and $Z^{10}$ is an organic group having at least two carbon atoms; wherein a, a', b, b', c, and c' independently represent integers of from 0 to 20; and wherein (a+a'), (b+b'), and (c+c') are, independently, integers of from 0 to 20, with the proviso that (a+a'), (b+b'), and (c+c') are not simultaneously 0.

In a further aspect, a, a', b, b', c, and c' independently represent integers of from 0 to 20, for example, from 0 to 12, from 0 to 10, from 0 to 8, from 0 to 6, from 0 to 4, from 1 to 20, from 0 to 12, from 0 to 10, from 0 to 8, from 0 to 6, from 0 to 4, or from 1 to 20. Each of a, a', b, b', c, and c' can be the same as or different from the others of a, a', b, b', c, and c'. In a yet further aspect, (a+a'), (b+b'), and (c+c') are, independently, integers of from 0 to 20, with the proviso that (a+a'), (b+b'), and (c+c') are not simultaneously 0. For example, each of (a+a'), (b+b'), and (c+c') can be, independently, an integer of from 0 to 12, from 0 to 10, from 0 to 8, from 0 to 6, from 0 to 4, from 1 to 20, from 0 to 12, from 0 to 10, from 0 to 8, from 0 to 6, from 0 to 4, or from 1 to 20, including 1, 2, 3, 4, 5, 6, 7, 8, 9, 10, 11, 12, 13, 14, 15, 16, 17, 18, 19, and 20. It is understood that, in a polymer, the average for any of a, a', b, b', c, c', (a+a'), (b+b'), and (c+c') can be a non-integer.

In a further aspect, $Q^1$, $Q^2$, and $Q^3$ independently represent alkyl.

a. Radical-Polymerizable Groups

In one aspect, the processes of the invention produce compounds bearing at least one radical-polymerizable group, M, as disclosed herein. It is understood that a one radical-polymerizable group can undergo a polymerization reaction with other radical-polymerizable groups of other compounds of the invention or with radical-polymerizable groups of comonomers, thereby producing a polymer comprising a residue of a compound of the invention.

b. Linking Groups

In one aspect, the processes of the invention produce compounds bearing at least one linking group, L, as disclosed herein. In a further aspect, linking group, L, can be substituted by one or more functionalized groups. For example, L can be substituted by hydroxy groups, hydroxyalkyl groups, amino groups, aminoalkyl groups, amide groups, alkylamide groups, alkoxy groups, alkoxyalkyl groups, alkoxycarbonyl groups, alkoxycabonylalkyl groups or a combination of those functionalized groups. In a yet further aspect, L can be substituted by hydroxy groups or hydroxyalkyl groups. Specifically, in one aspect, L can be substituted by hydroxy groups.

In a further aspect, one or more $CH_2$ groups of linking group, L, can be replaced by one or more hetero atoms. For example, one or more $CH_2$ groups of L can be replaced by O, S, N—$R^L$, P—$R^L$ or a combination of those hetero atoms, wherein $R^L$ is substituted or unsubstituted $C_1$-$C_{20}$ alkyl groups or substituted or unsubstituted $C_6$-$C_{20}$ aryl groups and $R^L$ can be substituted by one or more functionalized groups and $CH_2$ groups of $R^L$ can be replaced by one or more hetero atoms. In a yet further aspect, one or more $CH_2$ groups of L can be replaced by O or N—$R^L$.

In a further aspect, L has the structure:

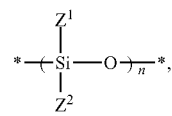

wherein G is hydrogen or a hydrolyzable group; wherein k represents an integer of 0 to 6; and wherein m represents an integer of 1 to 3 when k is 0, and represents an integer of from 1 to 20 when k is not 0, with the proviso that 1<3k+m<20.

In a further aspect, k is 1, and wherein m is from 1 to 7. In a yet further aspect, L is absent from the processes of the invention.

c. Siloxanyl Chains

In one aspect, the processes of the invention produce compounds optionally bearing siloxanyl chains having a general structure:

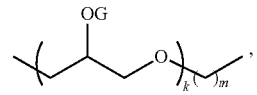

as disclosed herein.

d. Alkoxysilyl Compound

In one aspect, the processes of the invention relate to an alkoxysilyl compound having the structure:

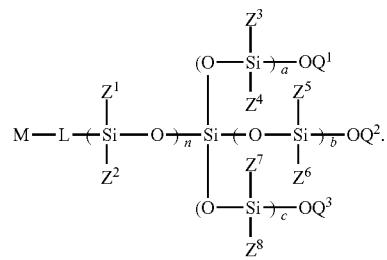

In a further aspect, $Q^1$, $Q^2$, and $Q^3$ independently represent hydrogen or a hydrolyzable group. For example, $Q^1$, $Q^2$, and $Q^3$ can independently represent an alkyl or aryl group including a methyl group, an ethyl group, a propyl group, a butyl group, a benzyl group, or a benzoyl group.

In a further aspect, $Z^1$ to $Z^8$ independently represent optionally substituted $C_1$-$C_{20}$ alkyl groups or optionally substituted $C_6$-$C_{20}$ aryl groups. The $C_1$-$C_{20}$ alkyl groups can be, for example, $C_1$-$C_{16}$ alkyl groups, $C_1$-$C_{12}$ alkyl groups, $C_1$-$C_8$ alkyl groups, $C_1$-$C_6$ alkyl groups, or $C_1$-$C_4$ alkyl groups. Examples include methyl, ethyl, n-propyl, i-propyl, n-butyl, s-butyl, i-butyl, t-butyl, n-pentyl, i-pentyl, s-pentyl, neopentyl, hexyl, heptyl, octyl, decyl, and dodecyl. The alkyl groups can be branched or linear. The $C_6$-$C_{20}$ aryl groups can be, for example, $C_6$-$C_{20}$ aryl groups, $C_6$-$C_{12}$ aryl groups, or $C_6$-$C_{10}$ aryl groups. Examples include phenyl, toluenyl, pyridinyl, and naphthalenyl.

n can be from 0 to 200, for example, from 0 to 100, from 0 to 50, from 0 to 25, from 0 to 12, from 0 to 10, from 0 to 6, from 0 to 4, from 1 to 200, from 1 to 100, from 1 to 50, from 1 to 25, from 1 to 12, from 1 to 10, from 1 to 6, or from 1 to 4. It is understood that, in a polymer, the average for n can be a non-integer.

In a further aspect, a, b, and c independently represent integers of from 0 to 20, for example, from 0 to 12, from 0 to 10, from 0 to 8, from 0 to 6, from 0 to 4, from 1 to 20, from 0 to 12, from 0 to 10, from 0 to 8, from 0 to 6, from 0 to 4, or from 1 to 20, including 1, 2, 3, 4, 5, 6, 7, 8, 9, 10, 11, 12, 13, 14, 15, 16, 17, 18, 19, and 20. Each of a, b, and c can be the same as or different from the others of a, b, and c. It is understood that, in a polymer, the average for any of a, b, and c can be a non-integer.

In a yet further aspect, the alkoxysilyl compound can have the structure:

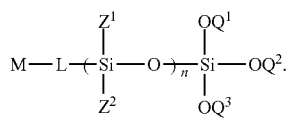

e. Silyl Halide Compound

In one aspect, silyl halides suitable for use in the process of the present invention have the structure:

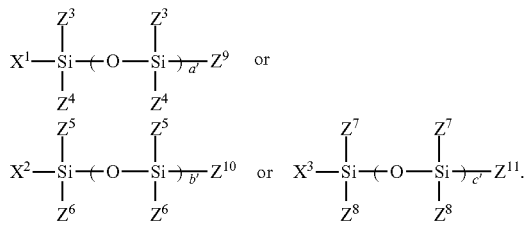

In one aspect, $X^1$, $X^2$, and $X^3$ independently represent a halogen selected from the group consisting of chlorine, bromine, and iodine.

In a further aspect, $Z^3$ to $Z^{11}$ independently represent optionally substituted $C_1$-$C_{20}$ alkyl groups or optionally substituted $C_6$-$C_{20}$ aryl groups. The $C_1$-$C_{20}$ alkyl groups can be, for example, $C_1$-$C_{16}$ alkyl groups, $C_1$-$C_{12}$ alkyl groups, $C_1$-$C_8$ alkyl groups, $C_1$-$C_6$ alkyl groups, or $C_1$-$C_4$ alkyl groups. Examples include methyl, ethyl, n-propyl, i-propyl, n-butyl, s-butyl, i-butyl, t-butyl, n-pentyl, i-pentyl, s-pentyl, neopentyl, hexyl, heptyl, octyl, decyl, and dodecyl. The alkyl groups can be branched or linear. The $C_6$-$C_{20}$ aryl groups can be, for example, $C_6$-$C_{20}$ aryl groups, $C_6$-$C_{12}$ aryl groups, or $C_6$-$C_{10}$ aryl groups. Examples include phenyl, toluenyl, pyridinyl, and naphthalenyl.

In a further aspect, a', b', and c' independently represent integers of from 0 to 20, for example, from 0 to 12, from 0 to 10, from 0 to 8, from 0 to 6, from 0 to 4, from 1 to 20, from 0 to 12, from 0 to 10, from 0 to 8, from 0 to 6, from 0 to 4, or from 1 to 20, including 1, 2, 3, 4, 5, 6, 7, 8, 9, 10, 11, 12, 13, 14, 15, 16, 17, 18, 19, and 20. Each of a', b', and c' can be the same as or different from the others of a', b', and c'. It is understood that, in a polymer, the average for any of a', b', and c' can be a non-integer.

In a further aspect, a silyl halide compound has the structure:

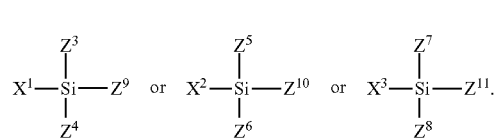

f. Reaction Conditions

Typically, an alkoxysilyl compound (e.g., trialkoxysilylalkylacrylate) and at least about three molar equivalents of a silyl halide (e.g., trialkylsilyl halide) are added to a mixture of water, alcohol, and an organic solvent. The trialkoxysilylalkylacrylate and the trialkylsilyl halide can be added separately or as a mixture and are typically added by way of dropping funnel. Such addition is typically performed while the mixture is agitated by, for example, stirring, shaking, or sonicating.

i. Reagents

In one aspect, an alkoxysilyl compound as disclosed herein, for example a trialkoxysilylalkylacrylate, can be used in connection with the disclosed methods. Typically, one molar equivalent of this reagent is used.

In one aspect, a silyl halide as disclosed herein, for example a trialkylsilyl halide, can be used in connection with the disclosed methods. Although one of ordinary skill in the art of organic synthesis can readily determine the relative amount of silyl halide to be used in a reaction, typically, at least three molar equivalents of the silyl halide, relative to the alkoxysilyl compound, are used. In a further aspect, when an excess is desired, four, five, six, or more molar equivalents can be used.

In one aspect, water can be used in connection with the disclosed methods. More specifically, water can be used in the mixture to which the alkoxysilyl compound and the silyl halide are added. In further aspects, the water is deionized water or distilled water. Typically, about 0.5 mL of water is used per 1 mmol of alkoxysilyl compound to be reacted; however, from about 0.1 mL to about 3.0 mL of water can be used per 1 mmol of alkoxysilyl compound. Without wishing to be bound by theory, it is believed that the water participates in hydrolysis of the alkoxysilyl compound, thereby forming a nucleophile, which then reacts with the silyl halide.

In one aspect, an alcohol can be used in connection with the disclosed methods. The alcohol can be, for example, methanol, ethanol, n-propanol, i-propanol, n-butanol, i-butanol, s-butanol, t-butanol, pentanol, hexanol, or other $C_7$-$C_{12}$ alcohol. In a further aspect, the alcohol is miscible with water. Typically, about 0.5 mL of alcohol is used per 1 mL of water in the mixture; however, from about 0.1 mL to about 3.0 mL of alcohol can be used per 1 mL of water.

In one aspect, an organic solvent can be used in connection with the disclosed methods. In various aspects, the organic solvent can be a hydrocarbon, including pentane, cyclopentane, hexane, cyclohexane, heptane, octane, nonane, or decane; an ether, including diethyl ether; or an amide, including dimethylformamide, dimethylformamide, dimethylacetamide, and diethylacetamide. In a further aspect, the organic solvent is selected so as to be immiscible with water. Typically, about 0.5 mL of organic solvent is used per 1 mL of water in the mixture; however, from about 0.1 mL to about 3.0 mL of organic solvent can be used per 1 mL of water.

ii. Temperature and Pressure

The addition is typically carried out at a temperature of from about 0° C. to about 10° C., for example, from about 0° C. to about 5° C. or from about 2° C. to about 3° C. That is, the mixture of water, alcohol, and an organic solvent is typically cooled before and/or during addition of the alkoxysilyl compound and the silyl halide. In a further aspect, the alkoxysilyl compound and/or the silyl halide are cooled before and/or during addition to a temperature of, for example, from about 0° C. to about 10° C., for example, from about 0° C. to about 5° C. or from about 2° C. to about 3° C. The addition can be conveniently carried out at atmospheric pressure (i.e., about 760 Torr).

iii. Time

In one aspect, the reaction is allowed to stir for a period from about 30 minutes to about 6 hours, for example, from about 1 hour to about 4 hours, or about 3 hours. One of ordinary skill in the art can readily determine completion of the reactions by monitoring consumption of starting materials (e.g., alkoxysilyl compound) by chromatographic methods (e.g., thin layer chromatography (TLC), high performance liquid chromatography (HPLC), or gas chromatography (GC)).

iv. Purification

Upon completion of the reaction, the product can be isolated by removal of the organic layer (i.e., organic solvent and components soluble therein) and disposal of the aqueous layer. The organic layer is typically washed one or more times with brine and then dried over anhydrous sodium sulfate. The crude product can then be filtered, concentrated, and purified by column chromatography (silica gel; hexane/ethyl acetate).

g. Hydrolysis-Resistant Silicone Compound Produced Thereby

Also disclosed are the products produced by the processes of the invention. In one aspect, the hydrolysis-resistant silicone compound produced by the process can have the structure:

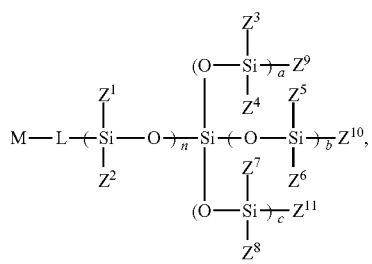

wherein M represents a radical-polymerizable group; wherein L represents an optionally substituted divalent $C_1$-$C_{20}$ organic group; wherein $Z^1$ to $Z^{11}$ independently represent optionally substituted $C_1$-$C_{20}$ alkyl groups or optionally substituted $C_6$-$C_{20}$ aryl groups, with the provisos that: at least one of $Z^3$, $Z^4$, and $Z^9$ is methyl, and at least one of $Z^3$, $Z^4$, and $Z^9$ is an organic group having at least two carbon atoms, at least one of $Z^5$, $Z^6$, and $Z^{10}$ is methyl, and at least one of $Z^5$, $Z^6$, and $Z^{10}$ is an organic group having at least two carbon atoms, and at least one of $Z^7$, $Z^8$, and $Z^{11}$ is methyl, and at least one of $Z^5$, $Z^6$, and $Z^{10}$ is an organic group having at least two carbon atoms; wherein n represents an integer of from 0 to 200; and wherein a, b, and c independently represent integers of from 0 to 20, with the proviso that a, b, and c are not simultaneously 0, as disclosed herein.

In various further aspects, the hydrolysis-resistant silicone compound can have the structure:

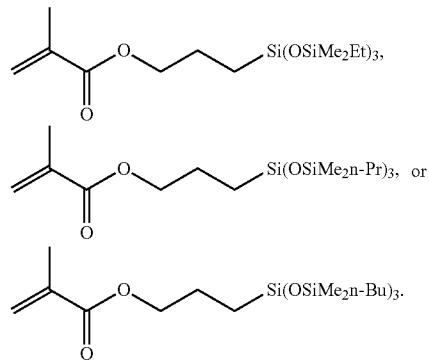

2. Reaction of Silyl Halide with a Silanol

In one aspect, the invention relates to a process for making a silicone compound having the structure:

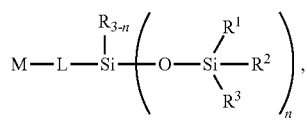

wherein M represents a radical-polymerizable group; wherein L represents an optionally substituted divalent $C_1$-$C_{20}$ organic group; wherein R, $R^1$, $R^2$, and $R^3$ independently represent optionally substituted $C_1$-$C_{20}$ alkyl groups or optionally substituted $C_6$-$C_{20}$ aryl groups, with the proviso that at least one of $R^1$, $R^2$, and $R^3$ is a group having at least 2 carbon atoms; and wherein n represents an integer of from 1 to 3, the process comprising the step of reacting a silyl halide having the structure:

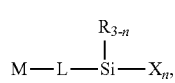

wherein X represents a halogen selected from the group consisting of chlorine, bromine, and iodine, with a silanol having the structure:

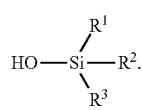

In a further aspect, water is substantially absent.

a. Radical-Polymerizable Groups

In one aspect, the processes of the invention produce compounds bearing at least one radical-polymerizable group, M. In one aspect, M is any moiety known to those of skill in the art that can undergo addition polymerization when exposed to a radical source, for example a radical initiator. In a further aspect, M can be an olefin. For example, M can be an alkene group, including an ethylene, a 1,3-butadiene moiety, or a styryl moiety. In a further aspect, M can be an acrylate. For example, M can be a residue of acrylic acid or a derivative thereof (e.g., alkyl acrylates) or residue of methacrylic acid or a derivative thereof (e.g., alkyl methacrylates). Specifically, in one aspect, M can be an acryloyl group or a methacryloyl group.

It is understood that a one radical-polymerizable group can undergo a polymerization reaction with other radical-polymerizable groups of other compounds of the invention or with radical-polymerizable groups of comonomers, thereby producing a polymer comprising a residue of a compound of the invention.

b. Linking Groups

In one aspect, the processes of the invention produce compounds bearing at least one linking group, L. In one aspect, L can be an optionally substituted divalent $C_1$-$C_{20}$ organic group, for example, a substituted or unsubstituted $C_1$-$C_{16}$ organic group, $C_1$-$C_{12}$ organic group, $C_1$-$C_8$ organic group, or a $C_1$-$C_4$ organic group. In a further aspect, linking group, L, can be a substituted or unsubstituted polyalkylene group. That is, L can be a group having two or more $CH_2$ groups linked to one another, represented by the formula —$(CH_2)_a$—, where "a" is an integer of from 1 to 20. Examples include methylene, ethylene, propylene, butylene, pentylene, and hexylene. The organic group can be branched or linear.

In a further aspect, L has the structure:

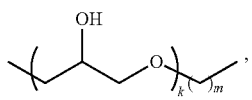

wherein k represents an integer of from 0 to 6; and wherein m represents an integer of from 1 to 3 when k is 0, and represents an integer of from 1 to 20 when k is not 0, with the proviso that $1 \leq 3k+m \leq 20$.

In a further aspect, k is 1, and wherein m is from 1 to 7. In a yet further aspect, k is 0, and m is from 1 to 3. In a still further aspect, L is absent from the processes of the invention.

c. Silyl Halide Compound

In one aspect, the processes of the invention relate to a silyl halide having the structure:

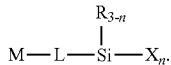

In one aspect, X represents a halogen selected from the group consisting of chlorine, bromine, and iodine.

In a further aspect, 3-n is an integer of from 0 to 2. That is, n represents an integer of from 1 to 3. For example, n can be 1, 2, or 3, while 3-n can be 2, 1, or 0.

In a yet further aspect, R represents an optionally substituted $C_1$-$C_{20}$ alkyl group or an optionally substituted $C_6$-$C_{20}$ aryl group. The $C_1$-$C_{20}$ alkyl group can be, for example, a $C_1$-$C_{16}$ alkyl group, a $C_1$-$C_{12}$ alkyl group, a $C_1$-$C_8$ alkyl group, a $C_1$-$C_6$ alkyl group, or a $C_1$-$C_4$ alkyl group. Examples include methyl, ethyl, n-propyl, i-propyl, n-butyl, s-butyl, i-butyl, t-butyl, n-pentyl, i-pentyl, s-pentyl, neopentyl, hexyl, heptyl, octyl, decyl, and dodecyl. The alkyl group can be branched or linear. The $C_6$-$C_{20}$ aryl group can be, for example, a $C_6$-$C_{20}$ aryl group, a $C_6$-$C_{12}$ aryl group, or a $C_6$-$C_{10}$ aryl group. Examples include phenyl, toluenyl, pyridinyl, and naphthalenyl.

d. Silanol

In one aspect, the processes of the invention relate to a silanol having the structure:

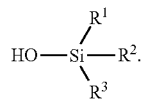

In a further aspect, n represents an integer of from 1 to 3. For example, n can be 1, 2, or 3.

In a yet further aspect, $R^1$, $R^2$, and $R^3$ independently represent optionally substituted $C_1$-$C_{20}$ alkyl groups or optionally substituted $C_6$-$C_{20}$ aryl groups. The $C_1$-$C_{20}$ alkyl groups can be, for example, $C_1$-$C_{16}$ alkyl groups, $C_1$-$C_{12}$ alkyl groups, $C_1$-$C_8$ alkyl groups, $C_1$-$C_6$ alkyl groups, or $C_1$-$C_4$ alkyl groups. Examples include methyl, ethyl, n-propyl, i-propyl, n-butyl, s-butyl, i-butyl, t-butyl, n-pentyl, i-pentyl, s-pentyl, neopentyl, hexyl, heptyl, octyl, decyl, and dodecyl. The alkyl groups can be branched or linear. The $C_6$-$C_{20}$ aryl groups can be, for example, $C_6$-$C_{20}$ aryl groups, $C_6$-$C_{12}$ aryl groups, or $C_6$-$C_{10}$ aryl groups. Examples include phenyl, toluenyl, pyridinyl, and naphthalenyl.

In a still further aspect, the silanol bears a sterically hindered terminal silicon group. That is, in one aspect, at least one of $R^1$, $R^2$, and $R^3$ is a group having at least 2 carbon atoms. That is, one or two or three of $R^1$, $R^2$, and $R^3$ can be a group having at least 2 carbon atoms, for example, an ethyl group, a propyl group, a butyl group, a pentyl group, a hexyl group, a heptyl group, an octyl group, a decyl group, a dodecyl group, a phenyl group, a toluenyl group, pyridinyl group, or a naphthalenyl group. In a yet further aspect, one of $R^1$, $R^2$, and $R^3$ is methyl, and at least one of $R^1$, $R^2$, and $R^3$ is ethyl, propyl, or butyl. In a still further aspect, two of $R^1$, $R^2$, and $R^3$ are methyl, and one of $R^1$, $R^2$, and $R^3$ is ethyl, propyl, or butyl.

e. Reaction Conditions

Typically, a silyl halide (e.g., trihalosilane) and at least one molar equivalents of a silanol (e.g., trialkylsilyl alcohol) are added to a mixture of an organic solvent and an amine solvent. The trialkoxysilylalkylacrylate and the trialkylsilyl halide are typically added separately and are typically added by way of dropping funnels. Such addition is typically performed while the mixture is agitated by, for example, stirring, shaking, or sonicating.

i. Reagents

In one aspect, a silyl halide as disclosed herein, for example a trihalosilane, can be used in connection with the disclosed methods. Typically, one molar equivalent of this reagent is used.

In one aspect, a silanol as disclosed herein, for example a trialkylsilyl alcohol, can be used in connection with the disclosed methods. Although one of ordinary skill in the art of organic synthesis can readily determine the relative amount of silanol to be used in a reaction, typically, at least one molar equivalent of the silanol, relative to the silyl halide, is used when the silyl halide is a monohalide. Typically, at least two molar equivalents of the silanol, relative to the silyl halide, are used when the silyl halide is a dihalide. Typically, at least three molar equivalents of the silanol, relative to the silyl halide, are used when the silyl halide is a trihalide. In a further aspect, when an excess is desired, four, five, six, or more molar equivalents can be used.

In one aspect, an organic solvent can be used in connection with the disclosed methods. In various aspects, the organic solvent can be an aromatic solvent, including benzene, toluene, naphthalene, ethylbenzene, pyridine, and dimethylaniline; a hydrocarbon, including pentane, cyclopentane, hexane, cyclohexane, heptane, octane, nonane, or decane; an ether, including diethyl ether; or an amide, including dimethylformamide, dimethylformamide, dimethylacetamide, and diethylacetamide. Typically, about 3.2 mL of organic solvent is used per 1 mmol of silyl halide; however, from about 2.0 mL to about 10.0 mL of organic solvent can be used per 1 mmol of silyl halide.

In one aspect, an amine solvent can be used in connection with the disclosed methods. Typically, the amine solvent is an aprotic amine, for example, and aromatic amine or a tertiary amine. Suitable amine solvents include pyridine, N-methylpiperidine, N-methylpyrrolidine, trimethylamine, triethylamine, and dimethylaniline. Typically, about 1 mmol of amine solvent is used per 1 mmol of silanol; however, from about 1 mmol to about 3.0 mmol of amine solvent can be used per 1 mmol of silanol.

ii. Temperature and Pressure

The addition can be conveniently carried out at room temperature (i.e., about 25° C.). The addition can be conveniently carried out at atmospheric pressure (i.e., about 760 Torr). In a further aspect, the reaction is heated before and/or during addition to a temperature of, for example, from about 25° C. to about 100° C., for example, from about 25° C. to about 50° C., from about 50° C. to about 75° C., or from about 75° C. to about 100° C. In a further aspect, the reaction is cooled before and/or during addition to a temperature of, for example, from about 0° C. to about 25° C., for example, from about 0° C. to about 5° C., from about 5° C. to about 10° C., from about 15° C. to about 20° C., or from about 20° C. to about 25° C.

iii. Time

In one aspect, the reaction is allowed to stir for a period from about 30 minutes to about 6 hours, for example, from about 1 hour to about 4 hours, or about 3 hours. One of ordinary skill in the art can readily determine completion of the reactions by monitoring consumption of starting materials (e.g., silyl halide) by chromatographic methods (e.g., thin layer chromatography (TLC), high performance liquid chromatography (HPLC), or gas chromatography (GC)).

iv. Purification

Upon completion of the reaction, the product solution is typically washed one or more times with water and then dried over anhydrous sodium sulfate. The crude product can then be filtered, concentrated, and purified by column chromatography (silica gel; hexane/ethyl acetate). The product can then be analyzed by, for example, GC to determine the ratio of the peak area of the silicone compound of interest to that of any by-product disiloxane.

f. Hydrolysis-Resistant Silicone Compound Produced Thereby

Also disclosed are the products produced by the processes of the invention. In one aspect, the hydrolysis-resistant silicone compound produced by the process can have the structure:

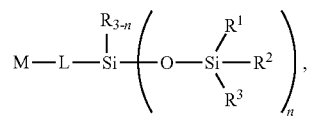

wherein M represents a radical-polymerizable group; wherein L represents an optionally substituted divalent $C_1$-$C_{20}$ organic group; wherein R, $R^1$, $R^2$, and $R^3$ independently represent optionally substituted $C_1$-$C_{20}$ alkyl groups or optionally substituted $C_6$-$C_{20}$ aryl groups, with the proviso that at least one of $R^1$, $R^2$, and $R^3$ is a group having at least 2 carbon atoms; and wherein n represents an integer of from 1 to 3, as disclosed herein.

3. Yield and Purity

In a further aspect, the processes of the invention can produce a compound having improved yield and/or purity as compared to conventional processes.

a. Improved Yield

The processes of the invention typically exhibit a greater yield than conventional processes. For example, in one aspect, the invention relates to a process for making a silicone compound having the structure:

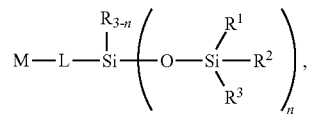

as disclosed herein, wherein the silicone compound is produced in a yield of at least about 10% by gas chromatography analysis. For example, the silicone compound can be produced in a yield of at least about 15%, at least about 20%, at least about 25%, at least about 30%, at least about 35%, at least about 40%, at least about 45%, or at least about 50% by gas chromatography analysis. In one aspect, water is substantially absent.

The yield of a process can be measured by, for example, gas chromatography (GC) analysis of the obtained crude products, as described in Example 5-1 and Comparative Example 5-1, infra. Comparison of the peak area attributable to the compound of the invention or the product of a process of the invention to the peak area attributable to side products, or to the total areas of all peaks in the chromatogram, can provide a measure of yield.

b. Improved Purity

In one aspect, a disiloxane compound having the structure:

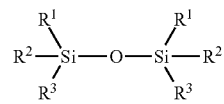

is present in an amount of from about 0% to about 20% by gas chromatography analysis. For example, a disiloxane can be present in an amount of from about 0% to about 15%, from about 0% to about 10%, from about 0% to about 5%, from about 0% to about 3%, from about 0% to about 3%, from about 0% to about 1%, or about 0% by gas chromatography analysis. In one aspect, a disiloxane compound is substantially absent.

Without wishing to be bound by theory, it is believed that the reaction of a silanol (or silanol precursor) with a sterically hindered silyl halide can result in an unsatisfactory amount of undesired disiloxane side-product. In contrast, again without wishing to be bound by theory, it is believed that the reaction of a sterically hindered silanol with a silyl halide can facilitate the production of desired hydrolysis-resistant silicone compounds, while minimizing the production of undesired disiloxane side-product.

D. CYCLIC SILOXANE MONOMERS

In a further aspect, the invention relates to cyclic siloxane monomers, polymers comprising residues of same, processes for making same, processes for polymerizing same. Silicone hydrogels comprising the polymer have improved thermal stability as compared to conventional silicone hydrogels. The cyclic siloxanes can be used as the sole source of silicone in silicone hydrogel-forming formulations, or can be used in combination with non-cyclic sloxanes such as TRIS, mPDMS, SiGMA, and others.

These monomers behave similarly to analogous non-cyclic analogues with respect to compatibility in the blends, contribution to oxygen permeability, and the like. For example, like SiGMA, C4-SiGMA can improve compatibility of silicone hydrogel forming blends, especially when high molecular weight internal wetting agents such as PVP are included in the blends.

1. Hydrolytic Stability in Conventional Silicone Hydrogels

Conventional silicone hydrogels have limited hydrolytic stability. When they are heated in water, it is common to observe an increase in the modulus of these materials. For example, the modulus of Purevision® (Bausch & Lomb) lenses increases from 155 to 576 psi when heated at 95° C. for one week. Under typical accelerated aging models, the useable shelf life of some silicone hydrogel lenses can be shortened by this modulus increase.

Without wishing to be bound by theory, it is believed that the cause of this increase in modulus is hydrolysis of terminal siloxane groups, followed by condensation reactions to form new siloxane bonds and to introduce new cross-links as shown below:

Further, the introduction of ionic carboxylate groups generally leads to substantially greater increase in moduli when heated in water. The increase in modulus of Purevision® (Bausch & Lomb) lenses is an example of this as they are made with VINAL (N-vinylcarboxy-β-alanine), a carboxylic acid-functional monomer. In one aspect, carboxylate groups can act as nucleophilic catalysts as shown below:

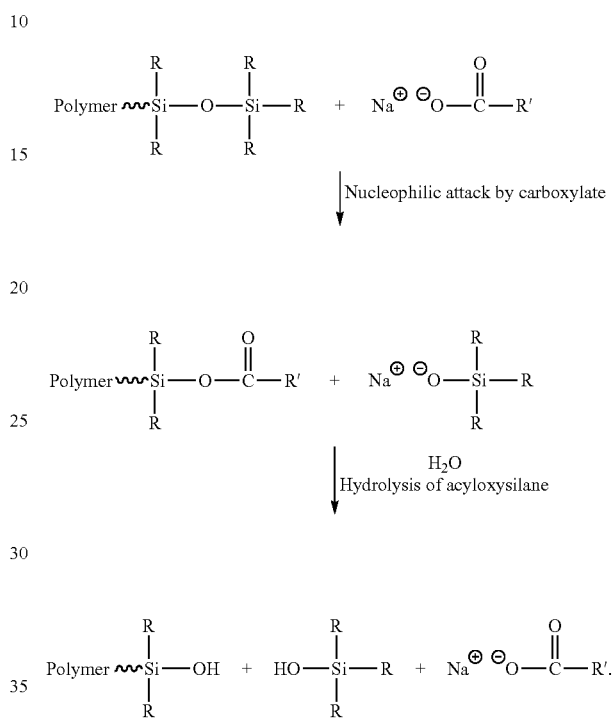

2. Improved Hydrolytic Stability

Monomers that contain small silicone rings and that do not contain terminal siloxane groups, such as trimethylsiloxane, typically condense to reform rings when siloxane bonds are hydrolytically cleaved, as shown below:

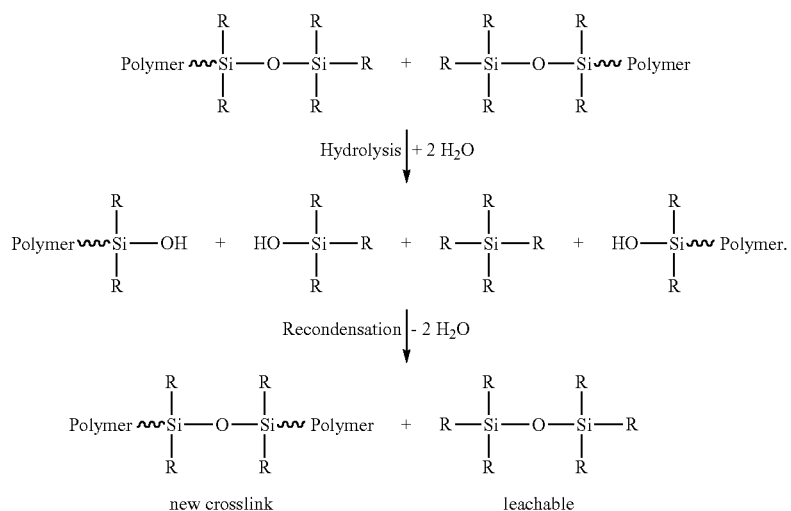

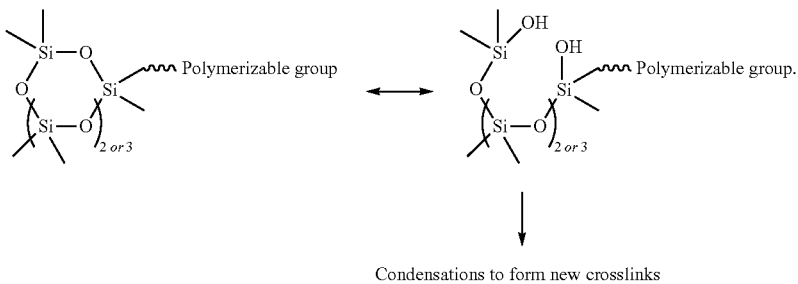

Condensations to form new crosslinks

In other words, the initial equilibrium favors internal condensation to reform the original cyclic siloxanes. Thus, new few new crosslinks are formed, and reduced modulus increase would be observed. Such monomers can be, for example, either cyclotetrasiloxanes or cyclopentasiloxanes.

In a cyclotrisiloxane methacrylate used to make a silicone hydrogel, the modulus was found to increase. Without wishing to be bound by theory, it is believed that this is because cyclotrisiloxanes are especially prone to undergo ring opening sue to ring strain. Thus, cyclotetrasiloxanes are even more stable.

3. Compounds

In one aspect, the compounds have the structure:

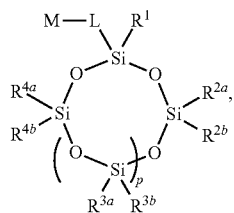

wherein p is 1, 2, or 3; wherein M represents a radical-polymerizable group; wherein L represents an optionally substituted divalent $C_1$-$C_{20}$ organic group; and wherein $R^1$, $R^{2a}$, $R^{2b}$, $R^{3a}$, $R^{3b}$, $R^{4a}$, and $R^{4b}$ independently represent optionally substituted $C_1$-$C_{20}$ alkyl groups or optionally substituted $C_6$-$C_{20}$ aryl groups. In a further aspect, $R^{2a}$=$R^{2b}$, $R^{3a}$=$R^{3b}$, and $R^{4a}$=$R^{4b}$.

Examples of preferred monomers are C4-TRIS and C4-SiMAA, shown below.

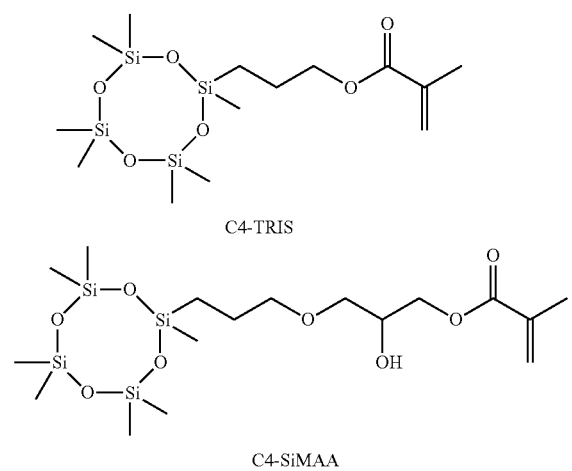

C4-TRIS

C4-SiMAA

That is, in one aspect, the compound has the structure:

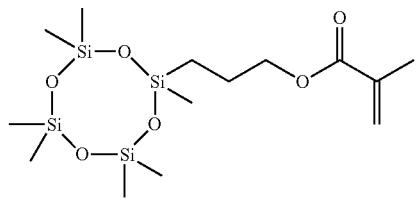

Also, in a further aspect, the compound has the structure:

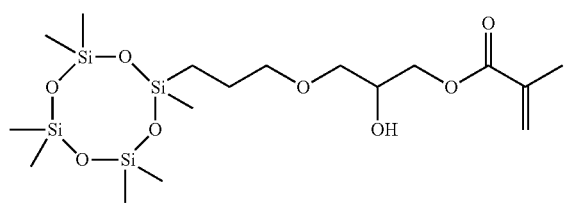

In various aspects, $R^1$, $R^{2a}$, $R^{2b}$, $R^{3a}$, $R^{3b}$, $R^{4a}$, and $R^{4b}$ are methyl.

a. Radical-Polymerizable Groups

In one aspect, the improved purity hydrolysis-resistant silicone compounds of the invention bear at least one radical-polymerizable group, M, as disclosed herein. In a further aspect, M is an acryloyl group, acryloyloxy group, a methacryloyl group, methacryloyloxy group, acrylamide group, methacrylamide group, N-vinylamide group, or styryl group. It is also understood that one radical-polymerizable group can undergo a polymerization reaction with other radical-polymerizable groups of other compounds of the invention or with radical-polymerizable groups of comonomers, thereby producing a polymer comprising a residue of a compound of the invention. Also disclosed are polymers comprising at least one residue of a compound of the disclosed cyclic siloxane monomers.

In a yet further aspect, the polymerizable group can be substituted with a compound having a functional group that can be chemically converted to a polymerizable group. For example, when allyl glycidyl ether is used, the resulting cyclic siloxane epoxide can be reacted with methacrylic acid to form C4-SiMAA.

b. Linking Groups

In one aspect, the improved purity hydrolysis-resistant silicone compounds of the invention optionally bear at least one linking group, L, as disclosed herein. In a further aspect, L is a divalent linking group having the structure:

wherein q is 1, 3, 4, 5, or 6. In a further aspect, q is 3.

In a further aspect, linking group, L, can be substituted by one or more functionalized groups. For example, L can be substituted by hydroxy groups, hydroxyalkyl groups, amino groups, aminoalkyl groups, amide groups, alkylamide groups, alkoxy groups, alkoxyalkyl groups, alkoxycarbonyl groups, alkoxycabonylalkyl groups or a combination of those functionalized groups. In a yet further aspect, L can be substituted by hydroxy groups or hydroxyalkyl groups. Specifically, in one aspect, L can be substituted by hydroxy groups.

In a further aspect, one or more $CH_2$ groups of linking group, L, can be replaced by one or more hetero atoms. For example, one or more $CH_2$ groups of L can be replaced by O, S, N—$R^L$, P—$R^L$ or a combination of those hetero atoms, wherein $R^L$ is substituted or unsubstituted $C_1$-$C_{20}$ alkyl groups or substituted or unsubstituted $C_6$-$C_{20}$ aryl groups and $R^L$ can be substituted by one or more functionalized groups and $CH_2$ groups of $R^L$ can be replaced by one or more hetero atoms. In a yet further aspect, one or more $CH_2$ groups of L can be replaced by O or N—$R^L$.

In a further aspect, L has the structure:

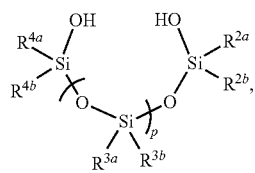

wherein G is hydrogen or a hydrolyzable group; wherein k represents an integer of 0 to 6; and wherein m represents an integer of 1 to 3 when k is 0, and represents an integer of from 1 to 20 when k is not 0, with the proviso that $1 \leq 3k+m \leq 20$.

4. Processes for Making

In one aspect, the invention relates to processes for making cyclic siloxane monomers. That is, in various aspects, disclosed are a process comprising the step of reacting n dihalosilyl compound with a siloxanyl diol compound and a. Reacting a Dihalosilyl Compound with a Siloxanyl Diol In one aspect, the invention relates to a process for making a cyclic siloxane monomer comprising the step of reacting a dihalosilyl compound having the structure:

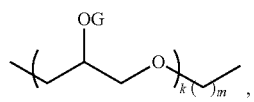

wherein M represents a radical-polymerizable group; wherein L represents an optionally substituted divalent $C_1$-$C_{20}$ organic group; and wherein $R^1$ represents an optionally substituted $C_1$-$C_{20}$ alkyl group or optionally substituted $C_6$-$C_{20}$ aryl group, with a siloxanyl diol compound having the structure:

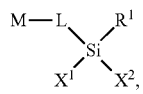

wherein p is 1, 2, or 3; and wherein $R^{2a}$, $R^{2b}$, $R^{3a}$, $R^{3b}$, $R^{4a}$, and $R^{4b}$ independently represent optionally substituted $C_1$-$C_{20}$ alkyl groups or optionally substituted $C_6$-$C_{20}$ aryl groups.

In a further aspect, the step can be represented by the following reaction:

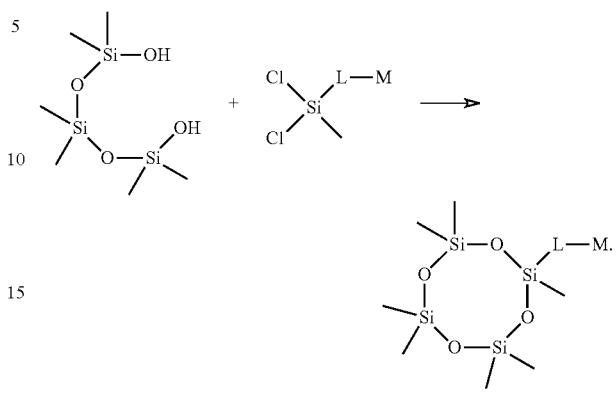

In a further aspect, the cyclic siloxane monomer has the structure:

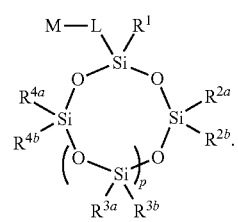

In a further aspect, the process further comprises the step of polymerizing the monomer.

Also disclosed are the product(s) of the process.

b. Hydrosilylating a Unsaturated Compound with a Cyclic Siloxanyl Silane Compound In one aspect, the invention relates to a process for making a cyclic siloxane monomer comprising the step of hydrosilylating a unsaturated compound having the structure:

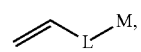

wherein M represents a radical-polymerizable group; wherein L represents an optionally substituted divalent $C_1$-$C_{20}$ organic group; and with a cyclic siloxanyl silane compound having the structure:

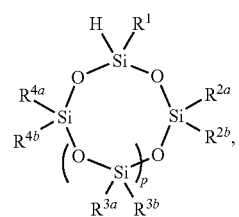

wherein p is 1, 2, or 3; and wherein $R^1$, $R^{2a}$, $R^{2b}$, $R^{3a}$, $R^{3b}$, $R^{4a}$, and $R^{4b}$ independently represent optionally substituted $C_1$-$C_{20}$ alkyl groups or optionally substituted $C_6$-$C_{20}$ aryl groups, in the presence of a transition metal catalyst. The cyclic siloxane starting material is typically commercially available.

The transition metal can be, for example, palladium or platinum.

In a further aspect, the step can be represented by the following reaction:

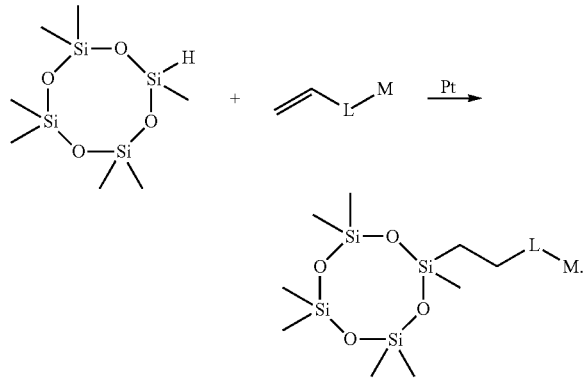

In a further aspect, the cyclic siloxane monomer has the structure:

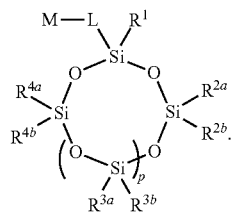

In a further aspect, the process further comprises the step of polymerizing the monomer.

Also disclosed are the product(s) of the process.

E. HYDROLYSIS-RESISTANT POLYMERS

In one aspect, the invention relates to a polymer comprising at least one residue of a compound of the invention or at least one residue of a product prepared by a process of the invention. That is, one or more subunits of a hydrolysis-resistant polymer comprise residues of a hydrolysis-resistant compound.

1. Copolymerization

In a further aspect, the polymer compositions of the invention can be provided as a copolymer. That is, the polymer comprises residues of a hydrolysis-resistant compound and residues of one or more additional monomers. For example, the compounds of the invention can be copolymerized with at least one comonomer, for example, a hydrophilic comonomer. Suitable hydrophilic comonomers include 2-hydroxyethyl methacrylate.

As the polymerizable materials which may be used for the copolymerization, monomers having a polymerizable carbon-carbon unsaturated bond such as (meth)acryloyl group, styryl group, allyl group, or vinyl group may be employed.

Preferred examples of such monomers include alkyl (meth)acrylates such as (meth)acrylic acid, itaconic acid, crotonic acid, cinnamic acid, vinylbenzoic acid, methyl (meth) acrylate and ethyl (meth)acrylate; polyfunctional (meth) acrylates such as polyalkylene glycol mono(meth)acrylate, polyalkylene glycol monoalkyl ether (meth)acrylate, polyalkylene glycol bis(meth)acrylate, trimethylolpropane tris (meth)acrylate, pentaerythritol tetrakis(meth)acrylate, polydimethyl siloxane having (meth)acryloxypropyl group at both ends, polydimethyl siloxane having (meth)acryloxypropyl group at one end and polydimethyl siloxane having a plurality of (meth)acryloyl groups in side chains; halogenated alkyl (meth)acrylates such as trifluoroethyl (meth)acrylate and hexafluoroisopropyl (meth)acrylate; hydroxyalkyl (meth)acrylates having hydroxyl group such as 2-hydroxyethyl (meth)acrylate and 2,3-dihydroxypropyl (meth)acrylate; (meth)acrylamides such as N,N-dimethylacrylamide, N,N-diethylacrylamide, N,N-di-n-propylacrylamide, N,N-diisopropylacrylamide, N,N-di-n-butylacrylamide, N-acryloylmorpholine, N-acryloylpiperidine, N-acryloylpyrrolidine and N-methyl(meth)acrylamide; N-vinyl-N-methyl acetamide, N-vinyl-N-ethyl acetamide, N-vinyl-N-ethyl formamide, N-vinyl formamide, aromatic vinyl monomers such as styrene, a-methylstyrene and vinylpyridine; maleimides; heterocyclic vinyl monomers such as N-vinylpyrrolidone; 3-[tris(trimethylsiloxy)silyl]propyl (meth)acrylate, 3-[bis (trimethylsiloxy)methylsilyl]propyl (meth)acrylate, 3-[(trimethylsiloxy)dimethylsilyl]propyl (meth)acrylate, 3-[tris (trimethylsiloxy)silyl]propyl (meth)acrylamide, 3-[bis (trimethylsiloxy)methylsilyl]propyl (meth)acrylamide, 3-[(trimethylsiloxy)dimethylsilyl]propyl (meth)acrylamide, [tris(trimethylsiloxy)silyl]methyl (meth)acrylate, [bis(trimethylsiloxy)methylsilyl]methyl (meth)acrylate, [(trimethylsiloxy)dimethylsilyl]methyl (meth)acrylate, [tris(trimethylsiloxy) silyl]methyl (meth)acrylamide, [bis(trimethylsiloxy) methylsilyl]methyl (meth)acrylamide, [(trimethylsiloxy) dimethylsilyl]methyl (meth)acrylamide, [tris (trimethylsiloxy)silyl]styrene, [bis(trimethylsiloxy) methylsilyl]styrene, [(trimethylsiloxy)dimethylsilyl]styrene, and polydimethyl siloxane having (meth)acryloxypropyl group at one end.

Further preferred examples of such monomers include 2-propenoic acid, 2-methyl-2-hydroxy-3-[3-[1,3,3,3-tetramethyl-1-[(trimethylsilyl)oxy]disiloxanyl]propoxy]propyl ester (SiGMA); monomethacryloxypropyl-terminated mono-n-butyl terminated polydimethylsiloxane (mPDMS; MW 800-1000 ($M_n$)); bis-3-acryloxy-2-hydroxypropyloxypropyl polydimethylsiloxane (acPDMS) (MW 1000 and 2000, acrylated polydimethylsiloxane from Gelest and Degussa, respectively); methacryloxypropyl-terminated polydimethylsiloxane (MW 550-700) from Gelest (maPDMS); and mono-(3-methacryloxy-2-hydroxypropyloxy) propyl terminated, mono-butyl terminated polydimethylsiloxane (mPDMS-OH).

Other silicone containing components suitable for use in this invention include those described in WO 96/31792 such as macromers containing polysiloxane, polyalkylene ether, diisocyanate, polyfluorinated hydrocarbon, polyfluorinated ether and polysaccharide groups. U.S. Pat. Nos. 5,321,108; 5,387,662; and 5,539,016 describe polysiloxanes with a polar fluorinated graft or side group having a hydrogen atom attached to a terminal difluoro-substituted carbon atom. US 2002/0016383 describes hydrophilic siloxanyl methacrylates containing ether and siloxanyl linkages and crosslinkable monomers containing polyether and polysiloxanyl groups.

2. Polymer Makeup

In one aspect, the polymer is a homopolymer. That is, substantially all of the monomer residues comprise residues of a hydrolysis-resistant compound.

In a further aspect, less than all of the monomer residues comprise residues of a hydrolysis-resistant compound. In a yet further aspect, at least 5% of the polymer comprises residues of a compound of the invention or residues of a product prepared by a process of the invention. For example, at least 10%, at least 15%, at least 20%, at least 25%, at least 30%, at least 35%, at least 40%, at least 45%, or at least 50% of the polymer can comprise residues of a compound of the invention or residues of a product prepared by a process of the invention.

In a further aspect, less than all of the mass of the polymer is provided by residues of a hydrolysis-resistant compound. In a yet further aspect, at least 5% of the mass of the polymer is provided by residues of a compound of the invention or residues of a product prepared by a process of the invention. For example, at least 10%, at least 15%, at least 20%, at least 25%, at least 30%, at least 35%, at least 40%, at least 45%, or at least 50% of the mass of the polymer can comprise residues of a compound of the invention or residues of a product prepared by a process of the invention.

F. HYDROLYSIS-RESISTANT COMPOSITIONS

While it is understood that the compounds of the invention and the products prepared by a process of the invention can be employed in any application known to those of skill in the art that is suitable for hydrolysis resistant compounds and/or compositions, the compounds, compositions, and products of processes of the invention can be employed as materials for the production of ophthalmic lenses, for example, contact lenses.

In one aspect, the invention relates to an ophthalmic lens comprising a polymer comprising at least one residue of a compound of the invention or a residue of a product of a process of the invention. In a further aspect, the invention relates to an contact lens comprising a polymer comprising at least one residue of a compound of the invention or a residue of a product of a process of the invention.

G. RESISTANCE TO HYDROLYSIS

Without wishing to be bound by theory, it is believed that compounds bearing sterically hindered terminal silicon groups have a greater resistance to hydrolysis conditions (e.g., acid hydrolysis) than compounds lacking sterically hindered terminal silicon groups.

In one aspect, the compounds of the invention, compositions of the invention, and products of processes of the invention are hydrolysis resistant. That is, compounds of the invention exhibit greater hydrolysis resistance than conventional compounds (i.e., compounds lacking a sterically hindered terminal silicon group). Also, a composition of the invention exhibits greater hydrolysis resistance when comprising a residue of a compound of the invention or a residue of a product of a process of the invention as compared to a similar composition in the absence of the residue of the compound or the product of a process.

The hydrolysis resistance of a compound or a product of a process can be measured by, for example, heating in the presence of alcohol, water, an acid (e.g., a carboxylic acid, such as acetic acid), and optionally, a polymerization inhibitor (e.g., 2,6-di-t-butyl-4-methylphenol). The mixture can be heated at a hydrolysis temperature (e.g., 80° C. or 90° C.) for a hydrolysis time (e.g., 136 hours or 168 hours), and the degree of decomposition can be determined by gas chromatography (GC) of the crude product. By comparing the peak area attributable to the compound or product being tested before subjecting to hydrolysis conditions to the peak area attributable to the compound or product being tested after subjecting to hydrolysis conditions, the proportion (percentage) of the compound or product being tested that survives hydrolysis conditions can be determined.

In various aspects, the compounds of the invention, the products of processes of the invention, and, thus, the compositions of the invention exhibit a hydrolysis resistance (approximately 5% by weight acetic acid in $H_2O$/2-propanol; 80° C.; 136 hours) of at least about 90%, at least about 92%, at least about 94%, at least about 95%, at least about 96%, at least about 97%, or at least about 98%. In contrast, comparative examples of conventional non-hydrolysis resistant compounds can exhibit a hydrolysis resistance (approximately 5% by weight acetic acid in $H_2O$/2-propanol; 80° C.; 136 hours) as low as approximately 46%.

In various further aspects, the compounds of the invention, the products of processes of the invention, and, thus, the compositions of the invention exhibit a hydrolysis resistance (approximately 5% by weight acetic acid in $H_2O$/n-butanol; 90° C.; 136 hours) of at least about 90%, at least about 92%, or at least about 94%. In contrast, comparative examples of conventional non-hydrolysis resistant compounds typically exhibit a hydrolysis resistance (approximately 5% by weight acetic acid in $H_2O$/n-butanol; 90° C.; 136 hours) of approximately 78%, approximately 61%, or even as low as approximately 35%,

H. COMPOSITIONS WITH SIMILAR FUNCTIONS

It is understood that the compositions disclosed herein have certain functions. Disclosed herein are certain structural requirements for performing the disclosed functions, and it is understood that there are a variety of structures which can perform the same function which are related to the disclosed structures, and that these structures will ultimately achieve the same result.

I. PREPARATION OF MOLDED PLASTICS

Molded plastics can be prepared from the material of the present invention by polymerizing the material for producing molded plastics according to the present invention alone or with one or more other materials.

For preparing the molded plastics, especially ophthalmic lenses, it can be preferred to use one or more copolymerizable materials having two or more polymerizable carbon-carbon unsaturated bonds in the molecule because good mechanical properties and good resistance to antiseptic solutions and washing solutions can be obtained. The percentage of the polymerizable material to be copolymerized, having two or more copolymerizable carbon-carbon unsaturated bonds in the molecule, based on the total monomers to be copolymerized, is preferably not less than about 0.01% by weight, more preferably not less than about 0.05% by weight, still more preferably not less than about 0.1% by weight.

1. Initiators

In the (co)polymerization for preparing the molded plastics, it is preferred to add a thermal polymerization initiator or photopolymerization initiator typified by peroxides and azo compounds for easily attaining polymerization. In cases where thermal polymerization is carried out, one having the optimum decomposition characteristics at the satisfactory reaction temperature is selected. In general, azo initiators and peroxide initiators having a 10 hour half-life temperature of from about 40° C. to about 120° C. are preferred. Examples of the photoinitiator include carbonyl compounds, peroxides, azo compounds, sulfur compounds, halogenated compounds and metal salts. These polymerization initiators can be used individually or in combination. The amount of the polymerization initiator(s) can be up to about 1% by weight based on the polymerization mixture.

2. Solvents

In (co)polymerizing the material for producing molded plastics according to the present invention, a polymerization solvent can be used. As the solvent, various organic and inorganic solvents can be employed. Examples of the solvents include water; alcoholic solvents such as methyl alcohol, ethyl alcohol, normal propyl alcohol, isopropyl alcohol, normal butyl alcohol, isobutyl alcohol, tert-butyl alcohol, ethylene glycol, diethylene glycol, triethylene glycol, tetraethylene glycol and polyethylene glycol; glycol ether solvents such as methyl cellosolve, ethyl cellosolve, isopropyl cellosolve, butyl cellosolve, propylene glycol monomethyl ether, diethylene glycol monomethyl ether, triethylene glycol monomethyl ether, polyethylene glycol monomethyl ether, ethylene glycol dimethyl ether, diethylene glycol dimethyl ether, triethylene glycol dimethyl ether and polyethylene glycol dimethyl ether; ester solvents such as ethyl acetate, butyl acetate, amyl acetate, ethyl lactate and methyl benzoate; aliphatic hydrocarbon solvents such as normal hexane, normal heptane and normal octane; alicyclic hydrocarbon solvents such as cyclohexane and ethylcyclohexane; ketone solvents such as acetone, methyl ethyl ketone and methyl isobutyl ketone; aromatic hydrocarbon solvents such as benzene, toluene and xylene; and petroleum solvents. These solvents can be used individually or two or more of these solvents can be used in combination.

3. Additives

The molded plastics may contain additional components, including, but not limited to UV absorbers, colorants, coloring agents, wetting agents, slip agents, pharmaceutical and nutraceutical components, compatibilizing components, antimicrobial compounds, release agents, combinations thereof and the like. Any of the foregoing may be incorporated in non-reactive, polymerizable, and/or copolymerized form.

4. Polymerization

As the method of polymerization of the material for producing molded plastics according to the present invention, and as the method of molding the plastics, known methods can be employed. For example, a method in which the material is once polymerized and molded into the shape of round bar or plate and the resulting round bar or plate is then processed into the satisfactory shape by cutting or the like, mold polymerization method and spin cast polymerization method can be employed.

As an example, a process for producing an ophthalmic lens by polymerizing the material composition containing the material for producing molded plastics according to the present invention by mold polymerization method will now be described.

First, a gap having a prescribed shape, between two mold parts is filled with the material composition and photopolymerization or thermal polymerization is carried out to shape the composition into the shape of the gap between the molds. The molds are made of a resin, glass, ceramics, metal, or the like. In case of photopolymerization, an optically transparent material is used, and a resin or glass is usually used. In case of producing an ophthalmic lens, a gap is formed between two mold parts facing each other, and the gap is filled with the material composition. Depending on the shape of the gap and on the properties of the material composition, a gasket may be used in order to give the ophthalmic lens a prescribed thickness and to prevent leakage of the material composition filled in the gap. The molds containing the gap filled with the material composition are then irradiated with an actinic radiation such as ultraviolet light, visible light or a combination thereof, or placed in an oven or bath to heat the material composition, thereby carrying out polymerization. The two polymerization methods may be employed in combination, that is, thermal polymerization may be carried out after photopolymerization, or photopolymerization may be carried out after thermal polymerization. In photopolymerization embodiment, a light containing ultraviolet light, such as the light from a mercury lamp or insect lamp is radiated for a short time (usually not longer than 1 hour). In cases where thermal polymerization is carried out, it is preferred to employ conditions in which the composition is slowly heated from room temperature to a temperature from about 60° C. to about 200° C. over a period of several hours to several tens hours, in view of the optical uniformity, high quality, and high reproducibility of the ophthalmic lens.

The molded plastics produced from the material of the present invention may preferably have a dynamic contact angle (during forward movement, immersion rate: about 0.1 mm/sec) of not more than about 130°, more preferably not more than about 120°, still more preferably not more than about 100°. The water content thereof is preferably from about 3% to about 0%, more preferably from about 5% to about 50%, still more preferably from about 7% to about 50%. From the viewpoint of the small burden to the wearer when the ophthalmic lens is used as a contact lens, the higher the oxygen permeability, the better. The oxygen permeability coefficient $[\times 10^{-11} \ (cm^2/sec)mLO_2/(mL \cdot hPa)]$ is preferably not less than about 50, more preferably not less than about 60, still more preferably not less than about 65. The tensile modulus of elasticity is preferably from about 0.01 to about 30 MPa, more preferably from about 0.1 to about 7 MPa. The tensile elongation is preferably not less than about 50%, more preferably not less than about 100%. Since a higher tensile elongation gives higher resistance to breakage, it is preferred that the molded plastics have a high tensile elongation.

5. Illustrative Uses

In one aspect, the compounds of the invention, compositions of the invention, and products of processes of the invention provide materials from which molded plastics having enhanced hydrolysis resistance can be produced. The molded plastics can be useful as drug adsorbents used for drug delivery and ophthalmic lenses such as contact lenses, intraocular lenses, artificial cornea and spectacle lenses. Among these, they are particularly suited for contact lenses.

In one aspect, the compounds and compositions of the invention can be used to provide a molded article comprising at least one of the compositions of the invention. In a further aspect, the compounds and compositions of the invention can be used to provide an ophthalmic lens comprising at least one of the compositions of the invention. In a yet further aspect, the compounds and compositions of the invention can be used to provide a contact lens comprising at least one of the compositions of the invention.

J. EXPERIMENTAL

The following examples are put forth so as to provide those of ordinary skill in the art with a complete disclosure and description of how the compounds, compositions, articles, devices and/or methods claimed herein are made and evaluated, and are not intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Analytical Methodology a. Gas Chromatography

In the gas chromatographic (GC) analysis, the identification of the peaks of the siloxanyl compounds represented by the Formula (A1) (wherein n is 0 to 12) is carried out by a separate gas chromatography mass spectrometry (GC-MS).

i. Apparatus and Parameters

Apparatus: Model GC6890 manufactured by HEWLETT-PACKARD or equivalent thereof. Detector: hydrogen flame ionization detector (FID). Column: Restek DB-1HT (30 m×0.25 mm×0.1 µm or equivalent). Carrier Gas: helium. Constant Flow: 1.0 mL/min. Amount of Applied Sample: 2.0 µL. Split Ratio: 30:1. Inlet Temperature: 300° C. Detector Temperature: 350° C. Solvent for Washing Autosampler: 2-propanol. Inlet Septum: Alltech 7/16" HT-X-11 or equivalent thereof ii. Temperature Program Initial Temperature: 100° C. Initial time: 2 min. Ramp: 15° C./min; Final Temp: 200° C.; hold for 0 min. Ramp: 5° C./min; Final Temp: 350° C.; hold for 0 min. Ramp: 15° C./min; Final Temp: 400° C.; hold for 15 min.

iii. Data Analysis Conditions

Slope Sensitivity: 50. Peak Width: 0.04. Area Reject: 1. Height Reject: 1. Integration Off: from 0 to 4 min.

iv. Preparation of Sample

About 50 µL of a sample is dissolved in 1.0 mL of 2-propanol. The sample and 2-propanol are directly placed in a vial for GC and mixed therein.

b. Gas Chromatography-Mass Spectrometry

Gas chromatography-mass spectrometry (GC-MS) analysis was carried out by carrying out the GC analysis under the conditions described above in the section <GC Analysis Conditions>, and by using as a mass spectrometer JMS-DX303 manufactured by JEOL.

c. Gel Permeation Chromatography

GPC was performed under the following conditions: Column: Shodex GPC K-801 and Shodex GPC K-802 manufactured by SHOKO CO., LTD. (each of them has an inner diameter of 8.0 mm and a length of 30 cm). The two columns were connected in series. Solvent: chloroform. Column Temperature: 40° C. Flow Rate: 1.0 mL/min. Apparatus: HLC-8022GPC manufactured by TOSOH CORPORATION, which is an integral apparatus combining a UV detector and a differential refractometer.

d. Matrix-Assisted Laser Desorption/Ionisation Time-of-Flight Mass Spectrometry

For matrix-assisted laser desorption/ionisation time-of-flight mass spectrometry (MALDI-TOF MS), AXIMA-CFR plus manufactured by SHIMADZU CORPORATION was used.

e. Oxygen Permeability Coefficient Testing

Figure 2:
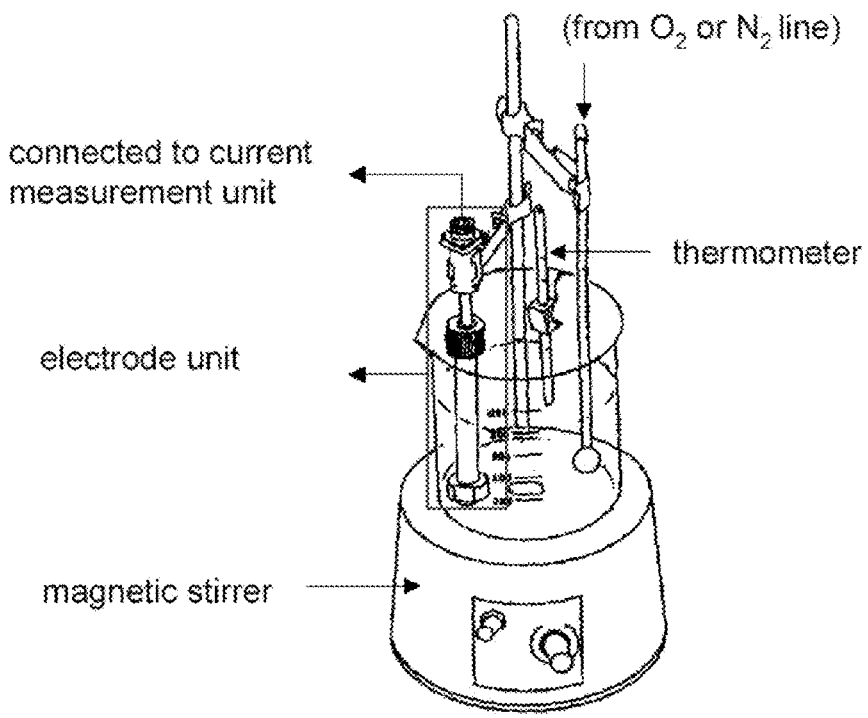
FIG. 2 shows an apparatus for oxygen permeability measurement.
Figure 3:
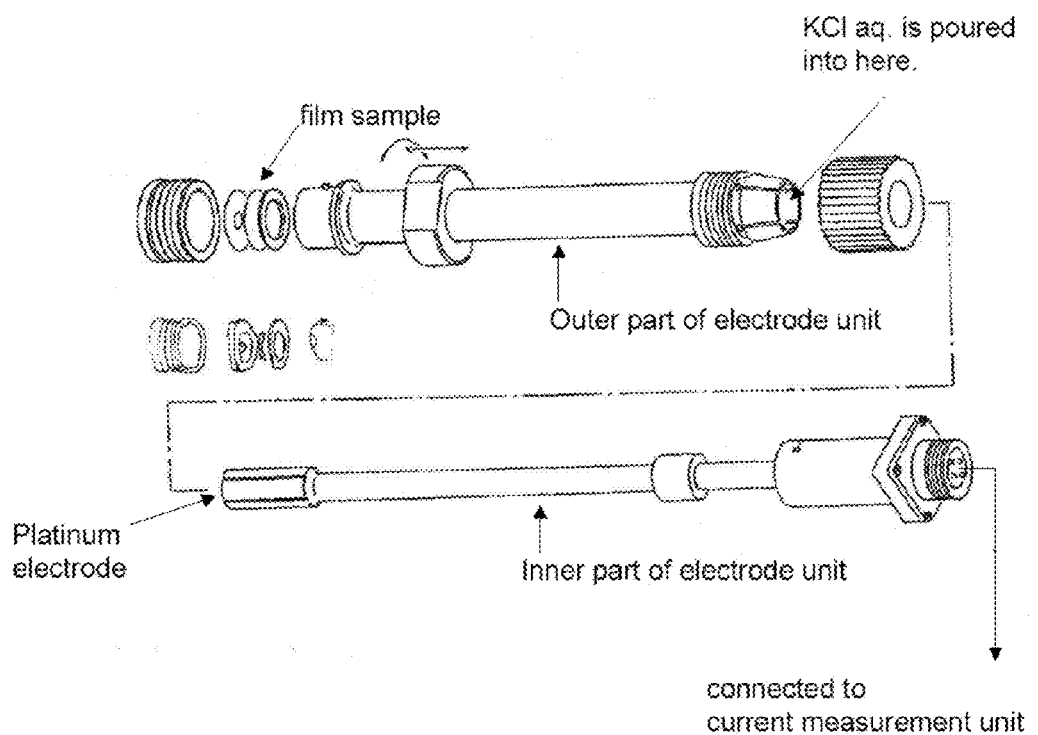
FIG. 3 shows the structure of an electrode unit used to measure oxygen permeability.
Figure 4:
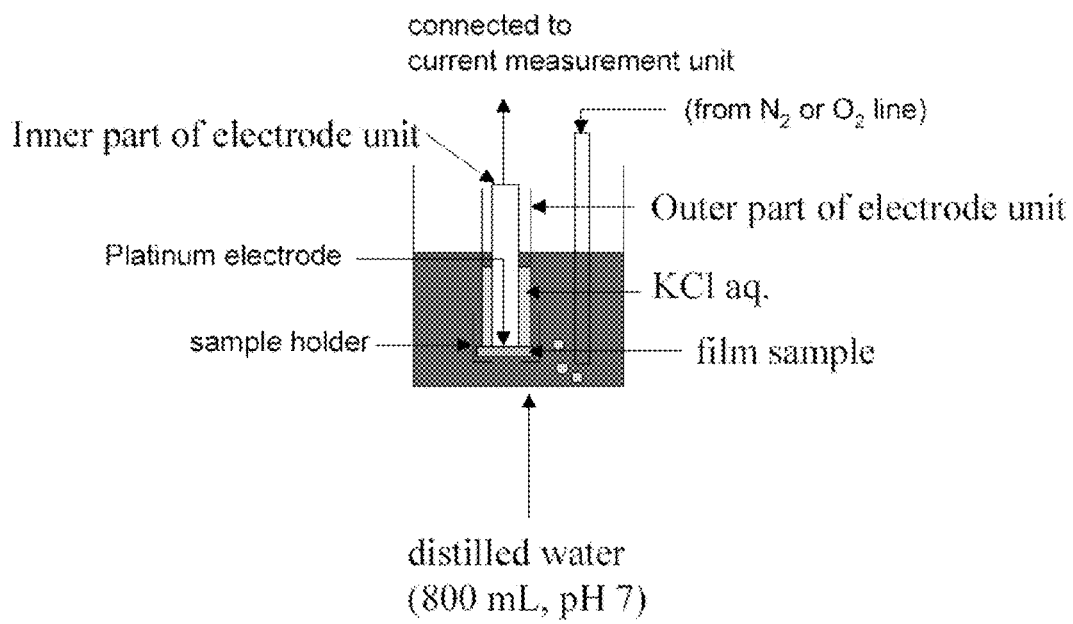
FIG. 4 shows a schematic of an oxygen permeability measurement setup.

A sample's oxygen permeability coefficient was determined by using a Seikaken-shiki film oxygen permeability meter manufactured by RIKA SEIKI KOGYO CO., LTD. The oxygen permeability coefficient of a sample in the form of a film was measured in water at 35° C. Four film samples with different thickness were prepared (0.1 mm, 0.2 mm, 0.3 mm, and 0.4 mm; diameter 16 mm). The four samples with different thickness were measured to determine Pm of every example (see FIG. 1). One of the samples was set at an electrode. 0.5 N KCl (aqueous) was poured into the electrode as an electrolytic solution (see FIGS. 2-4). The electrode was set in distilled water (pH=7, volume=800 ml). At first, the current under nitrogen bubbling (flow rate=100 mL/min.; electric current, i, is measured after it is in equilibrium) was measured in order to adjust zero. Then the current under oxygen bubbling was measured. R was calculated by the following formula: $R=(Ps \times N \times F \times A)/i$ [$cm^2$ sec mmHg/mL (STP)] (wherein Ps=760 mmHg (atmospheric pressure), N=4 (the number of electrons which involves a reaction at the electrode), F=96500 coulomb/mol (Faraday constant), A=area of the electrode ($cm^2$), i=measured current (uA)). R involves constant (not proportional) part, so plural measurement and plotting are necessary to determine Pm (see FIG. 1). R versus the thickness of the samples was plotted. The inverse of the slope is the oxygen permeability coefficient (Pm).

f. Moisture Content

A sample in the form of a film sizing about 10 mm×10 mm×0.2 mm was used. The sample was dried in a vacuum dryer at 40° C. for 16 hours, and the weight (Wd) of the sample was measured. Thereafter, the resulting sample was immersed in pure water at 40° C. in a thermostat bath overnight or more, and the moisture on the surface was wiped with Kimwipe, followed by measurement of the weight (Ww). The moisture content was calculated according to the following equation:

$$\text{Moisture Content}(\%) = 100 \times (Ww - Wd)/Ww$$

g. Tensile Modulus of Elasticity

Tensile Test: a sample in the form of a film sizing about 19.5 mm×15 mm×0.2 mm was used. The tensile modulus of elasticity was measured using Tensilon type RTM-100 manufactured by ORIENTEC. The speed of pulling was 100 mm/min and the distance between grips was 5 mm.

h. Optical Non-Uniformity

A sample molded into the form of contact lens was irradiated with light with a projector for photograph films to project its image on a screen, and the projected image on the screen was visually observed to evaluate the degree of optical non-uniformity. The evaluation was performed by classification into the following three ranks:

A: Distortion or turbidity is not observed at all.
B: Distortion or turbidity is observed very slightly.
C: Distortion or turbidity is observed.

2. Example 4-1

To a 50-mL eggplant type flask, 5 mL of water, 2.5 mL of methanol and 2.5 mL of hexane were added, and the resulting mixture was cooled to 2 to 3° C. under stirring on ice, followed by dropping a mixture of 2.48 g (10 mmol) of 3-trimethoxysilylpropyl methacrylate and 7.36 g (60 mmol) of ethyldimethylchlorosilane from a dropping funnel. After the dropping, the reaction solution was stirred at room temperature for 3 hours, and the disappearance of the starting materials was confirmed by gas chromatography (GC), which was regarded as the completion of the reaction. After completion of the reaction, stirring was stopped and the aqueous layer was discarded. The organic layer was transferred to a separation funnel, washed once with saturated aqueous sodium hydrogen carbonate solution and twice with saturated saline, and dried over anhydrous sodium sulfate. The resultant was filtered, and the solvent was evaporated with an evaporator. The obtained crude product was purified by column chromatography on 40 g of silica gel using 80 mL each of 20/1, 15/1, 10/1, 7/1, 4/1, and 4/1 mixtures of hexane/ethyl acetate as eluents, to obtain the silicone compound represented by the Formula (4p1) below.

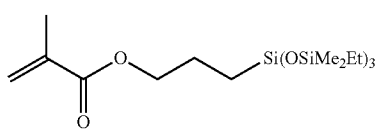
(4p1)

3. Example 4-2

The same synthesis and purification operations as in Example 4-1 were repeated except that n-propyldimethylchlorosilane was used in place of ethyldimethylchlorosilane to obtain the silicone compound represented by the Formula (4p2) below.

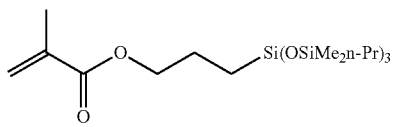
(4p2)

4. Example 4-3

The same synthesis and purification operations as in Example 4-1 were repeated except that n-butyldimethylchlorosilane was used in place of ethyldimethylchlorosilane to obtain the silicone compound represented by the Formula (4p3) below.

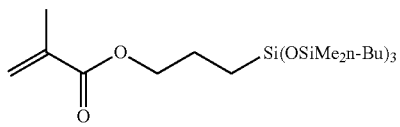
(4p3)

5. Comparative Example 4-1

The same synthesis and purification operations as in Example 4-1 were repeated except that triethylchlorosilane was used in place of ethyldimethylchlorosilane to obtain the silicone compound represented by the Formula (4r1) below.

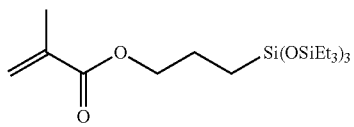
(4r1)

6. Comparative Example 4-2

The silicone compound represented by the Formula (4r2) below was synthesized by the method described in Japanese Laid-open Patent Application (Kokai) No. 56-22325. The obtained liquid was purified by silica gel column chromatography.

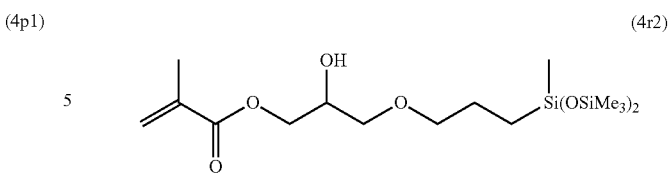
(4r2)

7. Example 4-5

Hydrolysis Resistance Test at 80° C.

The silicone compounds obtained in the above-described Example 4-1, Example 4-2, and Example 4-3 and Comparative Examples 4-1 and 4-2, as well as a commercially available silicone compound (Comparative Example 4-3) represented by the Formula (4r3) below were tested for their hydrolysis resistance in the presence of a carboxylic acid.

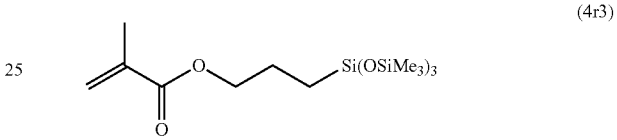
(4r3)

A solution of 0.1 g of the silicone compound, 3.90 g of 2-propanol, 0.24 g of acetic acid, 0.90 g of water and 2 mg of 2,6-di-t-butyl-4-methylphenol as a polymerization inhibitor was prepared. The obtained solution was heated in an oven at 80° C. for 168 hours, and the degree of decomposition was measured by gas chromatography (GC). Taking the GC area % of the peak of the silicone compound at the beginning (0 hr) of the test as 100, the ratios of the GC area % of the peak of the respective silicone compounds at 136 hours from the beginning of the test are shown in Table 1 in the column indicated by the heading "80° C.".

8. Example 4-6

Hydrolysis Resistance Test at 90° C.

The same test as in Example 4-5 above was repeated except that n-butanol having a higher boiling point than 2-propanol was used in place of 2-propanol. The results are shown in the column indicated by the heading "90° C." in Table 1.

TABLE 1

|  | 80° C. | 90° C. |
| --- | --- | --- |
| Example 4-1 | 97 | 92 |
| Example 4-2 | 94 | 90 |
| Example 4-3 | 98 | 94 |
| Comparative Example 4-1 | 98 | 78 |
| Comparative Example 4-2 | 46 | 35 |
| Comparative Example 4-3 | 73 | 61 |

9. Example 4-7

Preparation of Lens

The silicone compound (30 parts by weight) represented by Formula (p1) obtained in Example 4-1, N,N-dimethylacrylamide (40 parts by weight), polydimethylsiloxane of which terminals are methacrylated (molecular weight: about 1000, 30 parts by weight), triethylene glycol dimethacrylate (1 part by weight), methacrylic acid (1 part by weight) and Darocure 1173 (CIBA, 0.2 parts by weight) were mixed and stirred to obtain a uniform transparent monomer mixture. The monomer mixture was degassed under argon atmosphere. This monomer mixture was poured into a mold for contact lens, which was made of a transparent resin (poly(4-methyl-pent-1-ene), in a glove box under nitrogen atmosphere, and the mold was irradiated with light (1 mW/cm$^2$, 10 minutes) with a fluorescent lamp (e.g., of the type used for insect control) to polymerize the monomers, thereby obtaining a contact lens-shaped sample.

The obtained lens-shaped sample was subjected to hydration treatment and then immersed in 5 wt % aqueous polyacrylic acid (molecular weight: about 150,000) solution at 40° C. for 8 hours, thereby modifying the sample. After the modification treatment, the sample was sufficiently washed with purified water, and immersed in borate buffer (pH of 7.1 to 7.3) in a vial container. After sealing, the vial container was autoclaved for 30 minutes at 120° C. After allowing the vial container to cool, the lens-shaped sample was taken out from the vial container, and immersed in borate buffer (pH of 7.1 to 7.3). The obtained sample was transparent and free from turbidity, and suitable for use as a contact lens.

10. Example 5-1

To a 500-mL three-necked flask to which two dropping funnels were attached, 80 mL of toluene and 11.85 g (75 mmol) of pyridine were added. Under stirring the resulting mixture at the room temperature, a solution of 6.55 g (25 mmol) of 3-trichlorosilylpropyl methacrylate in 50 mL of toluene was dropped from a dropping funnel, while simultaneously dropping 9.90 g (75 mmol) of triethylsilanol from the other dropping funnel. After the dropping, the reaction solution was stirred at room temperature for 3 hours, and the disappearance of the starting materials was confirmed by gas chromatography (GC), which was regarded as the completion of the reaction. The reaction solution was washed with water, dried over anhydrous sodium sulfate, and the organic solvent was evaporated with an evaporator, thereby obtaining a liquid of a crude product. GC analysis of the obtained liquid revealed that the ratio of the peak area of the silicone compound of interest to that of a by-product disiloxane was as shown in Table 2.

The obtained liquid of a crude product was purified by column chromatography on silica gel in an amount of 40 g per 10 g of the obtained liquid using 80 mL each of 20/1, 15/1, 10/1, 7/1, 4/1, and 4/1 mixtures of hexane/ethyl acetate as eluents, to obtain the silicone compound represented by the Formula (5p1) below.

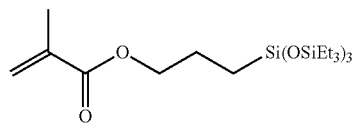
(5p1)

11. Comparative Example 5-1

To a 50-mL eggplant type flask, 5 mL of water, 2.5 mL of methanol and 2.5 mL of hexane were added, and the resulting mixture was cooled to 2 to 3° C. under stirring on ice, followed by dropping a mixture of 2.48 g (10 mmol) of 3-trimethoxysilylpropyl methacrylate and 7.36 g (60 mmol) of triethylchlorosilane from a dropping funnel. After the addition was complete, the reaction solution was stirred at room temperature for 3 hours, and the disappearance of the starting materials was confirmed by gas chromatography (GC), which was regarded as the completion of the reaction. After completion of the reaction, stirring was stopped, and the aqueous layer was discarded. The organic layer was transferred to a separation funnel, washed once with saturated aqueous sodium hydrogen carbonate solution and twice with saturated saline, and dried over anhydrous sodium sulfate. The resultant was filtered, and the solvent was evaporated with an evaporator. GC analysis of the obtained crude product revealed the ratio of the peak area of the silicone compound (5p1) to that of a by-product hexaethyldisiloxane was as shown in Table 2.

TABLE 2

|  | silicone compound (p1) | disiloxane | others |
| --- | --- | --- | --- |
| Example 5-1 | 67.2 | 2.7 | 30.1 |
| Comparative Example 5-1 | 1.9 | 76.3 | 21.8 |

12. Comparative Example 5-2

The same reaction procedures as in Comparative Example 5-1 were repeated except that trimethylchlorosilane was used in place of triethylchlorosilane. GC analysis of the obtained crude product revealed that 3-tris(trimethylsiloxy)silylpropyl methacrylate was obtained at a ratio of 69.8% in terms of GC area % as a major product.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A process for making a hydrolysis-resistant silicone compound having a sterically hindered terminal silicon group, the process comprising the step of reacting an alkoxysilyl compound having the structure:

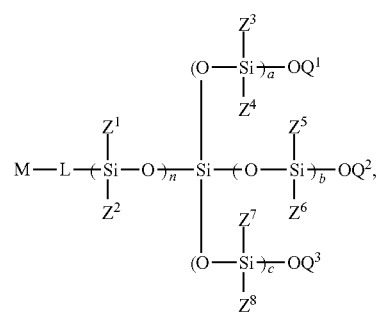

with one or more silyl halide compounds having the structure:

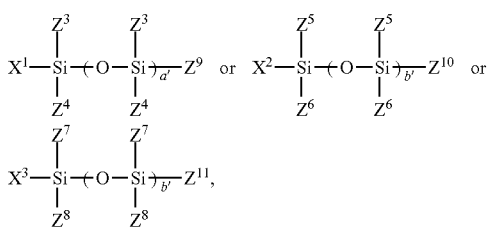

wherein $X^1$, $X^2$, and $X^3$ independently represent a halogen selected from the group consisting of chlorine, bromine, and iodine;

wherein M represents a radical-polymerizable group;

wherein L represents an optionally substituted divalent $C_1$-$C_{20}$ organic group;

wherein n represents an integer of from 0 to 200;

wherein $Q^1$, $Q^2$, and $Q^3$ independently represent hydrogen or a hydrolyzable group;

wherein $Z^1$ to $Z^{11}$ independently represent optionally substituted $C_1$-$C_{20}$ alkyl groups or optionally substituted $C_6$-$C_{20}$ aryl groups, with the provisos that:
- at least one of $Z^3$, $Z^4$, and $Z^9$ is methyl, and at least one is an organic group having at least two carbon atoms,
- at least one of $Z^5$, $Z^6$, and $Z^{10}$ is methyl, and at least one is an organic group having at least two carbon atoms, and
- at least one of $Z^7$, $Z^8$, and $Z^{11}$ is methyl, and at least one is an organic group having at least two carbon atoms;

wherein a, a', b, b', c, and c' independently represent integers of from 0 to 20; and wherein (a+a'), (b+b'), and (c+c') are, independently, integers of from 0 to 20, with the proviso that (a+a'), (b+b'), and (c+c') are not simultaneously 0.

2. The process of claim 1, wherein M is an acryloyloxy group, a methacryloyloxy group, acrylamide group, methacrylamide group, N-vinylamide group, or styryl group.

3. The process of claim 2, wherein M is an acryloyloxy group or a methacryloyloxy group.

4. The process of claim 1, wherein L has the structure:

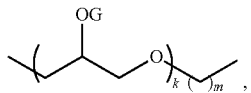

wherein G is hydrogen or a hydrolyzable group;

wherein k represents an integer of 0 to 6; and wherein m represents an integer of 1 to 3 when k is 0, and represents an integer of from 1 to 20 when k is not 0, with the proviso that 1≤3k+m≤20.

5. The process of claim 1, wherein $Q^1$, $Q^2$, and $Q^3$ independently represent alkyl.

6. The process of claim 1, wherein the alkoxysilyl compound has the structure:

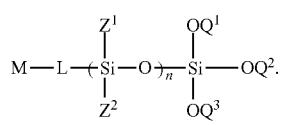

7. The process of claim 1, wherein the silyl halide compound has the structure:

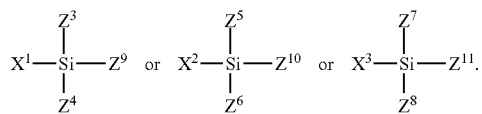

8. The process of claim 1, wherein the hydrolysis-resistant silicone compound has the structure:

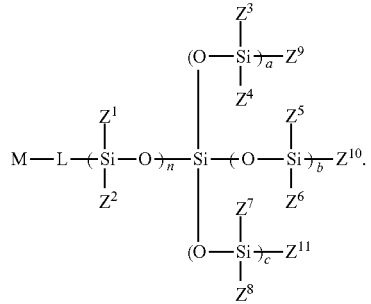

* * * * *